US009724864B2

(12) United States Patent
Cottone et al.

(10) Patent No.: US 9,724,864 B2
(45) Date of Patent: *Aug. 8, 2017

(54) BIOABSORBABLE POLYMERIC COMPOSITION AND MEDICAL DEVICE

(71) Applicant: ORBUSNEICH MEDICAL, INC., Fort Lauderdale, FL (US)

(72) Inventors: Robert J. Cottone, Davie, FL (US); G. Lawrence Thatcher, Chelmsford, MA (US)

(73) Assignee: OrbusNeich Medical, Inc., Fort Lauderdale, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/197,357

(22) Filed: Mar. 5, 2014

(65) Prior Publication Data

US 2015/0028513 A1    Jan. 29, 2015

Related U.S. Application Data

(63) Continuation of application No. 11/875,892, filed on Oct. 20, 2007, now Pat. No. 8,691,321.

(Continued)

(51) Int. Cl.
*A61F 2/06* (2013.01)
*B29C 47/00* (2006.01)
*A61F 2/915* (2013.01)
*A61L 31/04* (2006.01)
*A61L 31/14* (2006.01)

(Continued)

(52) U.S. Cl.
CPC .......... *B29C 47/0026* (2013.01); *A61F 2/915* (2013.01); *A61L 31/041* (2013.01); *A61L 31/048* (2013.01); *A61L 31/148* (2013.01); *B29C 47/0004* (2013.01); *A61F 2002/91591* (2013.01); *A61F 2230/0054* (2013.01); *B29K 2067/046* (2013.01); *B29K 2995/006* (2013.01);

(Continued)

(58) Field of Classification Search
CPC ...... A61F 2/86; A61F 2/06; A61F 2/82; A61F 31/10; A61F 2210/0004
USPC ...................... 623/1.38, 1.46; 427/2.24, 2.25
See application file for complete search history.

(56) References Cited

U.S. PATENT DOCUMENTS 4,057,537 A    11/1977 Sinclair
4,243,775 A    1/1981 Rosensaft et al.
(Continued)

FOREIGN PATENT DOCUMENTS

CN    1509315 A    6/2004
EP    0272902 A2    6/1988
(Continued)

OTHER PUBLICATIONS

"PolyLactic Acid", wikipedia.com, accessed Mar. 12, 2012, 6 pgs.
(Continued)

*Primary Examiner* — Cachet Sellman
(74) *Attorney, Agent, or Firm* — Leason Ellis LLP

(57) ABSTRACT

A method for fabricating an embodiment of a medical device comprising the steps of: preparing a biodegradable polymeric structure; coating the biodegradable polymeric structure with a polymeric coat including a pharmacological or biological agent; cutting the structure into patterns configured to allow for crimping of the cut structure and expansion of the cut structure after crimping into a deployed configuration.

5 Claims, 20 Drawing Sheets

Related U.S. Application Data

(60) Provisional application No. 60/862,433, filed on Oct. 20, 2006.

(51) Int. Cl.
*B29K 67/00* (2006.01)
*B29L 31/00* (2006.01)

(52) U.S. Cl.
CPC .............. *B29K 2995/0088* (2013.01); *B29L 2031/7532* (2013.01)

(56) References Cited

U.S. PATENT DOCUMENTS

| | | | |
|---|---|---|---|
| 4,300,565 A | 11/1981 | Rosensaft et al. | |
| 4,379,138 A | 4/1983 | Pitt et al. | |
| 4,650,488 A | 3/1987 | Bays et al. | |
| 4,655,777 A | 4/1987 | Dunn et al. | |
| 4,719,246 A | 1/1988 | Murdoch et al. | |
| 4,810,775 A | 3/1989 | Bendix et al. | |
| 4,916,193 A | 4/1990 | Tang et al. | |
| 4,938,763 A | 7/1990 | Dunn et al. | |
| 4,944,974 A | 7/1990 | Zachariades | |
| 4,968,317 A | 11/1990 | Tormala et al. | |
| 5,066,772 A | 11/1991 | Tang | |
| 5,085,629 A * | 2/1992 | Goldberg et al. ................. | 604/8 |
| 5,097,005 A | 3/1992 | Tietz | |
| 5,142,023 A | 8/1992 | Gruber et al. | |
| 5,145,945 A | 9/1992 | Tang et al. | |
| 5,185,408 A | 2/1993 | Tang et al. | |
| 5,225,129 A | 7/1993 | Van Den Berg | |
| 5,225,521 A | 7/1993 | Spinu | |
| 5,256,764 A | 10/1993 | Tang et al. | |
| 5,274,074 A | 12/1993 | Tang et al. | |
| 5,290,494 A | 3/1994 | Coombes et al. | |
| 5,322,925 A | 6/1994 | Muth et al. | |
| 5,342,395 A | 8/1994 | Jarrett et al. | |
| 5,378,792 A | 1/1995 | Sterzel | |
| 5,412,068 A | 5/1995 | Tang et al. | |
| 5,475,063 A | 12/1995 | Kaplan et al. | |
| 5,486,593 A | 1/1996 | Tang et al. | |
| 5,492,997 A | 2/1996 | Grijpma et al. | |
| 5,525,646 A | 6/1996 | Lundgren et al. | |
| 5,536,807 A | 7/1996 | Gruber et al. | |
| 5,578,325 A | 11/1996 | Domb et al. | |
| 5,665,428 A | 9/1997 | Cha et al. | |
| 5,665,831 A | 9/1997 | Neuenschwander et al. | |
| 5,670,161 A | 9/1997 | Healy et al. | |
| 5,691,424 A | 11/1997 | Suzuki et al. | |
| 5,716,396 A | 2/1998 | Williams, Jr. | |
| 5,739,176 A | 4/1998 | Dunn et al. | |
| 5,792,400 A | 8/1998 | Talja et al. | |
| 5,827,322 A | 10/1998 | Williams | |
| 5,834,582 A | 11/1998 | Sinclair et al. | |
| 5,849,374 A | 12/1998 | Gruber et al. | |
| 5,849,401 A | 12/1998 | El-Afandi et al. | |
| 5,916,950 A | 6/1999 | Obuchi et al. | |
| 5,925,061 A | 7/1999 | Ogi | |
| 5,948,016 A | 9/1999 | Jang | |
| 5,990,194 A | 11/1999 | Dunn et al. | |
| 6,033,433 A | 3/2000 | Her | |
| 6,107,453 A | 8/2000 | Zuccato et al. | |
| 6,165,217 A | 12/2000 | Hayes | |
| 6,221,958 B1 | 4/2001 | Shalaby et al. | |
| 6,228,111 B1 | 5/2001 | Tormala et al. | |
| 6,297,349 B1 | 10/2001 | Goldberg et al. | |
| 6,306,424 B1 | 10/2001 | Vyakarnam et al. | |
| 6,333,029 B1 | 12/2001 | Vyakarnam et al. | |
| 6,346,599 B1 | 2/2002 | Goldberg et al. | |
| 6,350,464 B1 | 2/2002 | Dang | |
| 6,352,667 B1 | 3/2002 | English | |
| 6,355,699 B1 | 3/2002 | Vyakarnam et al. | |
| 6,361,789 B1 | 3/2002 | Zuccato et al. | |
| 6,365,149 B2 | 4/2002 | Vyakarnam et al. | |
| 6,365,173 B1 | 4/2002 | Domb | |
| 6,413,539 B1 | 7/2002 | Shalaby | |
| 6,511,748 B1 | 1/2003 | Barrows | |
| 6,534,084 B1 | 3/2003 | Vyakarnam et al. | |
| 6,537,585 B1 | 3/2003 | Dang et al. | |
| 6,572,894 B2 | 6/2003 | Rossling et al. | |
| 6,607,548 B2 * | 8/2003 | Pohjonen et al. ............ | 606/230 |
| 6,730,772 B2 | 5/2004 | Shastri | |
| 6,740,731 B2 | 5/2004 | Bigg et al. | |
| 6,747,121 B2 | 6/2004 | Gogolewski | |
| 6,794,484 B2 | 9/2004 | Newman, Jr. et al. | |
| 6,916,483 B2 | 7/2005 | Ralph et al. | |
| 6,991,647 B2 | 1/2006 | Jadhav | |
| 7,001,328 B1 | 2/2006 | Barofsky et al. | |
| 7,112,417 B2 | 9/2006 | Vyakarnam et al. | |
| 7,160,592 B2 | 1/2007 | Rypacek et al. | |
| 7,264,641 B2 | 9/2007 | Prasad | |
| 7,291,166 B2 | 11/2007 | Cheng et al. | |
| 7,291,345 B2 | 11/2007 | Winterbottom et al. | |
| 7,297,102 B2 | 11/2007 | Smith et al. | |
| 7,326,245 B2 | 2/2008 | Rosenthal | |
| 2001/0000189 A1 | 4/2001 | Hayes | |
| 2001/0000352 A1 | 4/2001 | Hayes | |
| 2001/0012940 A1 | 8/2001 | Tunc | |
| 2001/0021871 A1 | 9/2001 | Stinson | |
| 2001/0029398 A1 | 10/2001 | Jadhav | |
| 2001/0033857 A1 | 10/2001 | Vyakarnam et al. | |
| 2001/0038854 A1 | 11/2001 | Hata et al. | |
| 2001/0043913 A1 | 11/2001 | Spaans et al. | |
| 2001/0044413 A1 * | 11/2001 | Pierce et al. .................... | 514/44 |
| 2001/0044514 A1 | 11/2001 | Baker et al. | |
| 2001/0044567 A1 | 11/2001 | Zamora et al. | |
| 2001/0051833 A1 | 12/2001 | Walter et al. | |
| 2002/0005600 A1 | 1/2002 | Ma | |
| 2002/0028911 A1 | 3/2002 | Barnette et al. | |
| 2002/0032488 A1 | 3/2002 | Brekke et al. | |
| 2002/0099434 A1 | 7/2002 | Buscemi et al. | |
| 2002/0106406 A1 | 8/2002 | McHugh et al. | |
| 2002/0123546 A1 | 9/2002 | Bigg et al. | |
| 2002/0137706 A1 | 9/2002 | Evans et al. | |
| 2002/0150604 A1 | 10/2002 | Yi et al. | |
| 2002/0151617 A1 | 10/2002 | Mao et al. | |
| 2002/0151650 A1 | 10/2002 | Pathak et al. | |
| 2002/0155092 A1 | 10/2002 | Leong et al. | |
| 2002/0161400 A1 | 10/2002 | Demopulos et al. | |
| 2002/0168338 A1 | 11/2002 | Baird | |
| 2002/0173595 A1 | 11/2002 | Pohjonen et al. | |
| 2002/0188347 A1 | 12/2002 | Mathis | |
| 2002/0192294 A1 | 12/2002 | Albayrak | |
| 2002/0192449 A1 | 12/2002 | Hobbs et al. | |
| 2003/0009004 A1 | 1/2003 | Nam et al. | |
| 2003/0014127 A1 | 1/2003 | Talja et al. | |
| 2003/0049320 A1 | 3/2003 | Bhagwatwar et al. | |
| 2003/0050426 A1 | 3/2003 | Shastri | |
| 2003/0050687 A1 | 3/2003 | Schwade et al. | |
| 2003/0060595 A1 | 3/2003 | Rafler et al. | |
| 2003/0060836 A1 | 3/2003 | Wang et al. | |
| 2003/0082148 A1 | 5/2003 | Ludwig et al. | |
| 2003/0083732 A1 | 5/2003 | Stinson | |
| 2003/0083745 A1 | 5/2003 | Pohjonen et al. | |
| 2003/0114637 A1 | 6/2003 | Gogolewski | |
| 2003/0134099 A1 | 7/2003 | Barrows | |
| 2003/0138493 A1 | 7/2003 | Dang | |
| 2003/0144570 A1 | 7/2003 | Hunter et al. | |
| 2003/0147934 A1 | 8/2003 | Hissink et al. | |
| 2003/0149474 A1 | 8/2003 | Becker | |
| 2003/0153965 A1 | 8/2003 | Supronowicz et al. | |
| 2003/0161881 A1 | 8/2003 | Hansen et al. | |
| 2003/0191449 A1 | 10/2003 | Nash et al. | |
| 2003/0195611 A1 | 10/2003 | Greenhalgh et al. | |
| 2003/0208259 A1 | 11/2003 | Penhasi | |
| 2003/0211135 A1 | 11/2003 | Greenhalgh et al. | |
| 2003/0212449 A1 | 11/2003 | cox | |
| 2003/0216496 A1 | 11/2003 | Mohanty et al. | |
| 2003/0219562 A1 | 11/2003 | Rypacek et al. | |
| 2003/0229391 A1 | 12/2003 | Thompson | |
| 2003/0229393 A1 * | 12/2003 | Kutryk et al. ............... | 623/1.46 |
| 2003/0236573 A1 | 12/2003 | Evans et al. | |
| 2004/0002580 A1 | 1/2004 | Newman, Jr. et al. | |
| 2004/0006146 A1 | 1/2004 | Evans et al. | |

(56) References Cited

U.S. PATENT DOCUMENTS

| | | |
|---|---|---|
| 2004/0006199 A1 | 1/2004 | Newman, Jr. et al. |
| 2004/0009226 A1 | 1/2004 | McHugh et al. |
| 2004/0013703 A1 | 1/2004 | Ralph et al. |
| 2004/0013730 A1 | 1/2004 | Saxena et al. |
| 2004/0014929 A1 | 1/2004 | Lendlein et al. |
| 2004/0024143 A1 | 2/2004 | Lendlein et al. |
| 2004/0029750 A1 | 2/2004 | Schudel et al. |
| 2004/0030380 A1 | 2/2004 | Shulze et al. |
| 2004/0030408 A1 | 2/2004 | Griffin et al. |
| 2004/0039441 A1 | 2/2004 | Rowland et al. |
| 2004/0054372 A1 | 3/2004 | Corden et al. |
| 2004/0058140 A1 | 3/2004 | Hobbs et al. |
| 2004/0071774 A1 | 4/2004 | Dang |
| 2004/0088044 A1 | 5/2004 | Brown |
| 2004/0089602 A1 | 5/2004 | Heinrich et al. |
| 2004/0098090 A1 | 5/2004 | Williams |
| 2004/0137033 A1 | 7/2004 | Calhoun et al. |
| 2004/0138738 A1 | 7/2004 | Stinson |
| 2004/0156906 A1 | 8/2004 | Ding et al. |
| 2004/0157967 A1 | 8/2004 | Ito |
| 2004/0161442 A1 | 8/2004 | Zamora et al. |
| 2004/0210218 A1 | 10/2004 | Dixon et al. |
| 2004/0214983 A1 | 10/2004 | Tobita et al. |
| 2004/0215218 A1 | 10/2004 | Demopulos et al. |
| 2004/0220660 A1 | 11/2004 | Shanley et al. |
| 2004/0247644 A1 | 12/2004 | Bratt et al. |
| 2004/0249442 A1 | 12/2004 | Fleming |
| 2004/0253290 A1 | 12/2004 | Kim et al. |
| 2004/0260318 A1 | 12/2004 | Hunter et al. |
| 2005/0001358 A1 | 1/2005 | Nakazawa et al. |
| 2005/0008672 A1 | 1/2005 | Winterbottom et al. |
| 2005/0021131 A1 | 1/2005 | Venkatraman et al. |
| 2005/0025808 A1 | 2/2005 | Herrmann et al. |
| 2005/0042253 A1 | 2/2005 | Farrar et al. |
| 2005/0058632 A1 | 3/2005 | Hendrick et al. |
| 2005/0112171 A1 | 5/2005 | Tang et al. |
| 2005/0112172 A1 | 5/2005 | Pacetti |
| 2005/0118238 A1 | 6/2005 | Zhu et al. |
| 2005/0119720 A1 | 6/2005 | Gale et al. |
| 2005/0123588 A1 | 6/2005 | Zhu et al. |
| 2005/0131528 A1 | 6/2005 | Buscemi et al. |
| 2005/0136259 A1 | 6/2005 | Mohanty et al. |
| 2005/0142163 A1 | 6/2005 | Hunter et al. |
| 2005/0147562 A1 | 7/2005 | Hunter et al. |
| 2005/0147643 A1 | 7/2005 | Hunter et al. |
| 2005/0161857 A1 | 7/2005 | Coombes et al. |
| 2005/0161859 A1 | 7/2005 | Miller et al. |
| 2005/0165142 A1 | 7/2005 | Nishimura et al. |
| 2005/0165206 A1 | 7/2005 | Rafler et al. |
| 2005/0169958 A1 | 8/2005 | Hunter et al. |
| 2005/0171299 A1 | 8/2005 | Shalaby |
| 2005/0175665 A1 | 8/2005 | Hunter et al. |
| 2005/0181011 A1 | 8/2005 | Hunter et al. |
| 2005/0186261 A1 | 8/2005 | Avelar et al. |
| 2005/0187605 A1 | 8/2005 | Greenhalgh et al. |
| 2005/0196420 A1 | 9/2005 | Zucherman et al. |
| 2005/0202067 A1 | 9/2005 | Lendlein et al. |
| 2005/0209603 A1 | 9/2005 | Zucherman et al. |
| 2005/0232966 A1 | 10/2005 | Hughes et al. |
| 2005/0238722 A1 | 10/2005 | Pathak et al. |
| 2005/0240137 A1 | 10/2005 | Zhu et al. |
| 2005/0244353 A1 | 11/2005 | Lendlein et al. |
| 2005/0244475 A1 | 11/2005 | Edelman et al. |
| 2005/0244538 A1 | 11/2005 | Andersen et al. |
| 2005/0245637 A1 | 11/2005 | Hossainy et al. |
| 2005/0246021 A1 | 11/2005 | Ringeisen et al. |
| 2005/0249697 A1 | 11/2005 | Uhrich et al. |
| 2005/0260247 A1 | 11/2005 | Ralph et al. |
| 2005/0271701 A1 | 12/2005 | Cottone et al. |
| 2005/0281856 A1 | 12/2005 | McGlohorn et al. |
| 2005/0283229 A1 | 12/2005 | Dugan et al. |
| 2005/0288771 A1 | 12/2005 | Majercak |
| 2006/0004437 A1 | 1/2006 | Jayaraman |
| 2006/0008504 A1 | 1/2006 | Kerr et al. |
| 2006/0018942 A1 | 1/2006 | Rowe et al. |
| 2006/0025649 A1 | 2/2006 | Smith et al. |
| 2006/0040894 A1 | 2/2006 | Hunter et al. |
| 2006/0041102 A1* | 2/2006 | Hossainy et al. ............ 528/354 |
| 2006/0047095 A1 | 3/2006 | Pacetti |
| 2006/0051455 A1 | 3/2006 | Andersen et al. |
| 2006/0062821 A1 | 3/2006 | Simhambhatla et al. |
| 2006/0067908 A1 | 3/2006 | Ding |
| 2006/0074191 A1 | 4/2006 | Desnoyer et al. |
| 2006/0083767 A1 | 4/2006 | Deusch et al. |
| 2006/0093771 A1 | 5/2006 | Rypacek et al. |
| 2006/0115449 A1 | 6/2006 | Pacetti |
| 2006/0140892 A1 | 6/2006 | Lendlein et al. |
| 2006/0147491 A1 | 7/2006 | Dewitt et al. |
| 2006/0154195 A1 | 7/2006 | Mather et al. |
| 2006/0160985 A1 | 7/2006 | Pacetti et al. |
| 2006/0177495 A1 | 8/2006 | Allen et al. |
| 2006/0178477 A1 | 8/2006 | Neuenschwander |
| 2006/0204738 A1 | 9/2006 | Dubrow et al. |
| 2006/0224226 A1 | 10/2006 | Huang et al. |
| 2006/0233887 A1 | 10/2006 | Day |
| 2006/0240078 A1 | 10/2006 | Jenkins et al. |
| 2006/0246108 A1 | 11/2006 | Pacetti et al. |
| 2006/0258834 A1 | 11/2006 | Van Der Wal et al. |
| 2006/0265048 A1* | 11/2006 | Cheng et al. ............... 623/1.15 |
| 2006/0269586 A1 | 11/2006 | Pacetti |
| 2006/0271170 A1 | 11/2006 | Gale et al. |
| 2006/0276345 A1 | 12/2006 | Todd et al. |
| 2006/0292198 A1 | 12/2006 | Dalal et al. |
| 2007/0003592 A1 | 1/2007 | Hissink |
| 2007/0009465 A1 | 1/2007 | Lendlein et al. |
| 2007/0009606 A1 | 1/2007 | Serdy et al. |
| 2007/0010831 A1 | 1/2007 | Romero-Ortega et al. |
| 2007/0020469 A1 | 1/2007 | Wood et al. |
| 2007/0027554 A1 | 2/2007 | Biran et al. |
| 2007/0032857 A1 | 2/2007 | Schmid |
| 2007/0034615 A1 | 2/2007 | Kleine |
| 2007/0043426 A1 | 2/2007 | Abbate |
| 2007/0071879 A1 | 3/2007 | Rypacek et al. |
| 2007/0071926 A1 | 3/2007 | Rypacek et al. |
| 2007/0087033 A1 | 4/2007 | Sigg et al. |
| 2007/0101578 A1 | 5/2007 | Shirazi |
| 2007/0114211 A1 | 5/2007 | Reynolds et al. |
| 2007/0116739 A1 | 5/2007 | Calhoun et al. |
| 2007/0117959 A1 | 5/2007 | Shastri et al. |
| 2007/0123977 A1 | 5/2007 | Cottone et al. |
| 2007/0128723 A1 | 6/2007 | Cottone et al. |
| 2007/0129789 A1 | 6/2007 | Cottone et al. |
| 2007/0134305 A1 | 6/2007 | Zilberman |
| 2007/0135578 A1 | 6/2007 | Mather |
| 2007/0141107 A1 | 6/2007 | Kutryk et al. |
| 2007/0149640 A1 | 6/2007 | Andjelic et al. |
| 2007/0149724 A1 | 6/2007 | Pacetti et al. |
| 2007/0151961 A1 | 7/2007 | Kleine et al. |
| 2007/0155943 A1 | 7/2007 | Yang et al. |
| 2007/0191963 A1 | 8/2007 | Winterbottom et al. |
| 2007/0198040 A1 | 8/2007 | Buevich et al. |
| 2007/0202148 A1 | 8/2007 | Ringeisen et al. |
| 2007/0224245 A1 | 9/2007 | Ameer et al. |
| 2007/0231362 A1 | 10/2007 | Perez et al. |
| 2007/0231365 A1 | 10/2007 | Wang et al. |
| 2007/0233232 A1 | 10/2007 | St. Germain |
| 2007/0238167 A1 | 10/2007 | Perez et al. |
| 2007/0253996 A1 | 11/2007 | Bin et al. |
| 2007/0254012 A1 | 11/2007 | Ludwig et al. |
| 2007/0275020 A1 | 11/2007 | Lendlein et al. |
| 2008/0051866 A1 | 2/2008 | Chen |
| 2008/0247987 A1 | 10/2008 | Liggins et al. |

FOREIGN PATENT DOCUMENTS

| | | |
|---|---|---|
| EP | 0401844 | 6/1990 |
| EP | 0709420 A2 | 5/1996 |
| EP | 0809981 A1 | 12/1997 |
| EP | 0999227 A2 | 5/2000 |
| EP | 1064958 A1 | 1/2001 |
| EP | 1138336 A1 | 10/2001 |
| EP | 1334990 A1 | 8/2003 |
| EP | 1374921 A1 | 1/2004 |
| EP | 1375557 A1 | 1/2004 |

(56) References Cited

FOREIGN PATENT DOCUMENTS

| | | |
|---|---|---|
| EP | 1382628 A1 | 1/2004 |
| EP | 1452191 A2 | 9/2004 |
| EP | 1462131 A1 | 9/2004 |
| EP | 1695718 A2 | 8/2006 |
| EP | 1728811 A1 | 12/2006 |
| EP | 1764118 A2 | 3/2007 |
| WO | WO 9003768 A1 | 4/1990 |
| WO | WO 9116368 A1 | 10/1991 |
| WO | WO 9204393 A1 | 3/1992 |
| WO | WO 9215340 A1 | 9/1992 |
| WO | WO 9309765 A1 | 5/1993 |
| WO | WO 9411441 | 5/1994 |
| WO | WO 9526762 A1 | 10/1995 |
| WO | WO 9619519 A1 | 6/1996 |
| WO | WO 9705193 A1 | 2/1997 |
| WO | WO 9711724 A1 | 4/1997 |
| WO | WO 9715287 A1 | 5/1997 |
| WO | WO 9715389 A1 | 5/1997 |
| WO | WO 9902201 A1 | 1/1999 |
| WO | WO 9910403 A1 | 3/1999 |
| WO | WO 9910404 A1 | 3/1999 |
| WO | WO 0113819 A2 | 3/2001 |
| WO | WO 0142333 A2 | 6/2001 |
| WO | WO 0185224 A1 | 11/2001 |
| WO | WO 0207749 A2 | 1/2002 |
| WO | WO 0231037 A1 | 4/2002 |
| WO | WO 0245685 A2 | 6/2002 |
| WO | WO 02092691 A1 | 11/2002 |
| WO | WO 03000766 A1 | 1/2003 |
| WO | WO 03020330 A2 | 3/2003 |
| WO | WO 03033042 A1 | 4/2003 |
| WO | WO 03034940 A2 | 5/2003 |
| WO | WO 03051328 A1 | 6/2003 |
| WO | WO 03055469 A1 | 7/2003 |
| WO | WO 03066705 A1 | 8/2003 |
| WO | WO 03068289 A1 | 8/2003 |
| WO | WO 2004028269 A1 | 4/2004 |
| WO | WO 2004028583 A2 | 4/2004 |
| WO | WO 2004045653 A2 | 6/2004 |
| WO | WO 2004053112 A1 | 6/2004 |
| WO | WO 2004069918 A2 | 8/2004 |
| WO | WO 2004080332 A2 | 9/2004 |
| WO | WO 2004091435 A2 | 10/2004 |
| WO | WO 2004108180 A1 | 12/2004 |
| WO | WO 2004110315 A1 | 12/2004 |
| WO | WO 2004112854 A1 | 12/2004 |
| WO | WO 2005002596 A1 | 1/2005 |
| WO | WO 2005013891 A2 | 2/2005 |
| WO | WO 2005027988 A2 | 3/2005 |
| WO | WO 2005039489 A2 | 5/2005 |
| WO | WO 2005041811 A2 | 5/2005 |
| WO | WO 2005051316 A2 | 6/2005 |
| WO | WO 2005051445 A1 | 6/2005 |
| WO | WO 2005051452 A2 | 6/2005 |
| WO | WO 2005061617 A1 | 7/2005 |
| WO | WO 2005065079 A2 | 7/2005 |
| WO | WO 2005074913 A2 | 8/2005 |
| WO | WO 2005110437 A2 | 11/2005 |
| WO | WO 2005114323 A2 | 12/2005 |
| WO | WO 2005117836 A2 | 12/2005 |
| WO | WO 2005123155 A2 | 12/2005 |
| WO | WO 2006002381 A1 | 1/2006 |
| WO | WO 2006020922 A2 | 2/2006 |
| WO | WO 2006020994 A2 | 2/2006 |
| WO | WO 2006023672 A2 | 3/2006 |
| WO | WO 2006026325 A2 | 3/2006 |
| WO | WO 2006044890 A2 | 4/2006 |
| WO | WO 2006053836 A1 | 5/2006 |
| WO | WO 2006060235 A2 | 6/2006 |
| WO | WO 2006066572 A2 | 6/2006 |
| WO | WO 2006066575 A1 | 6/2006 |
| WO | WO 2006069010 A2 | 6/2006 |
| WO | WO 2006071520 A2 | 7/2006 |
| WO | WO 2006073631 A1 | 7/2006 |
| WO | WO 2006074391 A2 | 7/2006 |
| WO | WO 2006074406 A2 | 7/2006 |
| WO | WO 2006078356 A1 | 7/2006 |
| WO | WO 2006111578 A1 | 10/2006 |
| WO | WO 2006128704 A1 | 12/2006 |
| WO | WO 2006130440 A1 | 12/2006 |
| WO | WO 2006135479 A2 | 12/2006 |
| WO | WO 2007019439 A2 | 2/2007 |
| WO | WO 2007041593 A2 | 4/2007 |
| WO | WO 2007041972 A1 | 4/2007 |
| WO | WO 2007059253 A2 | 5/2007 |
| WO | WO 2007084609 A2 | 7/2007 |
| WO | WO 2007085702 A1 | 8/2007 |
| WO | WO 2007092559 A2 | 8/2007 |
| WO | WO 2007115018 A2 | 10/2007 |
| WO | WO 2007115245 A2 | 10/2007 |
| WO | WO 2007117222 A1 | 10/2007 |
| WO | WO 2007117499 A2 | 10/2007 |
| WO | WO 2007126598 A2 | 11/2007 |
| WO | WO 2007126599 A2 | 11/2007 |
| WO | WO 2007132294 A2 | 11/2007 |
| WO | WO 2007132295 A2 | 11/2007 |
| WO | WO 2007143116 A2 | 12/2007 |
| WO | WO 2008011175 A2 | 1/2008 |

OTHER PUBLICATIONS

"The Glass Transition", Penn State University, 1-30, http://www.personal.psu.edu/irh1/PDF/Giass%20Temperature.pdf (last visited Sep. 26, 2012).

Tsuji, "Poly(lactide) stereocomplexes: formation, structure, properties, degradation, and applications", Macromol Biosci (Jul. 2005), 5(7):569-97.

Zhang; et al., "Preparation of linear low-density polyethylene by the in situ copolymerization of ethylene with an iron oligomerization catalyst and rac-ethylene bis(indenyl) zirconium (IV) dichloride", Journal of Polymer Science Part A: Polymer Chemistry (Mar. 2005), 43(5):984-993.

Amecke; et al., "Resorbable Polyesters: Composition, Properties, Applications", Clinical Materials (1992), 10:47-50.

Baimark; et al., "Synthesis and characterization ofpoly(L-lactideco-e-caprolactone) (B)-poly(L-lactide) (A) ABA block copolymers", Polym. Adv. Technol. (2005), 16:332-337.

Baimark; et al., "Synthesis, characterization and melt spinning ofa block colpolymer of L-lactide and s-caprolactone for potential use as an absorbable monofilament surgical suture", Journal of Materials Science: Materials in Medicine (2005), 16:699-707.

Bigg, "Polylactide Copolymers: Effect of Copolymer Ratio and End Capping on Their Properties", Advances in Polymer Technolo!!V (2005), 24(2):69-82.

Broz; et al., "Structure and mechanical properties ofpoly(d,l-lactic acid)/poly(e-caprolactone) blends", Biomaterials (2003), 24:4181-4190.

Cohn; et al., "Designing Biodegradable multiblock PCL/PLA thermoplastic elastomers", Biomaterials (2005), 26:2297-2305.

Dell'Erba; et al., "Immiscible polymer blends of semicrystalline biocompatible components: thermal properties and phase morphology analysis of PLLA/PCL blends", Polymer (2001), 42:7831-7840.

Feng; et al., "Synthesis and evaluation of biodegradable block copolymers ofs-caprolactone and DL-lactide", Journal of Polymer Science: Polymer Letters Edition (1983), 21(8):593-600.

Feng; et al., "Synthesis and drug controlled release of block copolymers ofpoly(L-lactide) with poly(D,L-lactide) and related monomers", Macromol. Symp. (1997), 118:625-630.

GE; et al., "Preparation, Characterization, and Drug Release Behaviors of Drug-Loaded ϵ-Caprolactone/L-lactide Copolymer Nanoparticles", Journal of Applied Polymer Science (2000), 75:874-882.

Grijpmaa; et al., "(Co)polymers of L-lactide, 1: Synthesis, thermal properties and hydrolytic degradation", Macromol. Chem. Phys. (1994), 195:1633-1647.

Hamley; et al., "Crystallization in Poly(L-lactide)-b-poly(-caprolactone) Double Crystalline Diblock Copolymers: A Study

(56) References Cited

OTHER PUBLICATIONS

Using X-ray Scattering, Differential Scanning Calorimetry, and Polarized Optical Microscopy", Macromolecules (2005), 38:463-472.
Hamley; et al., "Melt Structure and its Transformation by Sequential Crystallization of the Two Blocks within Poly(L-lactide)-block-Poly(s-caprolactone) Double Crystalline Diblock Copolymers", Macromol. Chem. Phys. (2006), 207:941-953.
Ho; et al., "Crystallization-Induced Orientation for Microstructures of Poly(L-lactide)-b- poly( -caprolactone) Diblock Copolymers", Macromolecules (2003), 36:9085-9092.
Kim; et al., "Effect of P(LLA-co-sCL) on the Compatibility and Crystallization Behavior of PCL/PLLA Blends", Journal of Applied Polymer Science (2000), 77:226-231.
Kim; et al., Synthesis and crystallization behavior of poly(L-lactide)-block(ecaprolactone) copolymer, Polymer (2001), 42:7429-7441.
Kuriyama; et al., "Compatibility and biodegradation of poly(lactic acid)-polycaprolactone blend systems", Nippon Setchaku Gakkai (2000), 38:173-176.
Lee; et al., "Surface Structure and Stereocomplex Formation ofEnantiomeric Polylactide Blends Using Poly(dimethyl siloxane) as a Probe Polymer", Macromol. Symp. (2006), 239:91-96.
Li; et al., "Synthesis of tadpole-shaped copolyesters based on living macrocyclic poly(s- caprolactone)", Polymer (2006), 47(26):8406-8413.
Lim; et al., "Stereocomplex Formation between Enantiomeric PLA-PEG- PLATriblock Copolymers: Characterization and Use as Protein-Delivery Microparticulate Carriers", Journal of Applied Polymer Science (2000), 75:1615-1623.
Lostocco; et al., "The effects of primary structure on the degradation ofpoly(s- caprolactone)/poly(L-Lactide) block copolymers", Polymer Degradation and Stability (1998), 59:303-307.
Lostocco; et al., "The Synthesis and Characterization of Polyesters Derived From L-Lactide and Variably-Sized Poly(Caprolactone)", Polymer Modification (1997), 45-57.
Lu; et al., "Shape memory property ofpoly(l-lactide-co—caprolactone) copolymers", Materials Science and Engineering A (2006), 438-440:857-861.
Maglio; et al., "Thermal properties of di- and triblock copolymers ofpoly(L-lactide) with poly(oxyethylene) or poly(s -caprolactone)", Polymer (2003), 44:369-375.
Maglio; et al., "Immiscible Poly(L-lactide)/Poly(s-caprolactone) Blends: Influence of the Addition ofa Poly(L-lactide)-Poly(oxyethylene) Block Copolymer on Thermal Behavior and Morphology", Macromol. Chem. Phys. (2004), 205:946-950.
Na; et al., "Compatibilization Effect of Poly(s-caprolactone)-b-poly(ethyleneglycol) Block Copolymers and Phase Morphology Analysis in Immiscible Poly(lactide)/Poly(s- caprolactone) Blends", Biomacromolecules (2002), 3:1179-1186.
Pensec; et al., "Stereocomplex formation in enantiomeric diblock and triblock copolymers of poly (s-caprolactone) and polylactide", Polymer Bulletin (2000), 45:373-380.
Piao; et al., "Synthesis and Characterization of Poly(s-caprolactone)-Poly(L-lactide) Diblock Copolymers with an Organic Amino Calcium Catalyst", Journal of Applied Science (2006), 102:2654-2660.
Portinha; et al., "Influence of Preparation Conditions on the Self-Assembly by Stereocomplexation of Polylactide Containing Diblock Copolymers", Macromolecules (2004), 37:3401-3406.
Lopez-Rodriguez; et al., "Crystallization, Morphology, and Mechanical Behavior of Polylactide/Poly(s-caprolactone) Blends", Polymer Engineering and Science (2006), 1299-1308.
Slivniak; et al., "Stereocomplexes ofEnantiomeric Lactic Acid and Sebacic Acid Ester-Anhydride Triblock Copolymers", Biomacromolecules (2002), 3:754-760.
Stevels; et al., "Well defined block copolymers ofs-caprolactone and L-lactide using Y5(µ-0)(0iPr)13a) as an initiator", Macromol. Chem. Phys. (1995), 196:1153-1161.
Stevels; et al., "Stereocomplex formulation in ABA triblock copolymers of poly(lactide) (A) and poly(ethylene glycol) (B)", Macromol. Chem. Phys. (1995), 196:3698-3694.
Tamura; et al., "Synthesis of Poly(Methylacrylate-b-s-Caprolactone) and Application to Compatibilizer for Poly(L-Lactide)/Poly(s-Caprolactone) Blend System", Materials Transactions (2005), 46(12):2668-2672.
Teng; et al., "Synthesis and Characterization of Poly(L-lactic acid)-Poly(s-caprolactone) Multiblock Copolymers by Melt Polycondensation", Journal of Polymer Science: Part A: Polymer Chemistry (2004), 42:5045-5053.
Tsuji; et al., "Enhanced Crystallization of Poly(L-lactide-co-s-caprolactone) During Storage at Room Temperature", Journal of Applied Polymer Science (2000), 76:947-953.
Tsuji; et al., "Blends of aliphatic polyesters. Part 7. Effects ofpoly(L-lactide-co-E—caprolactone) on morphology, structure, crystallization, and physical properties of blends of poly(L-lactide) and poly(E—caprolactone)", Polymer International (2003), 52:269-275.
Wang; et al., "Synthesis, Sequential Crystallization and Morphological Evolution of Well-Defined Star-Shaped Poly(s-caprolactone)-b-poly(L-lactide) Block Copolymers", Macromol. Chem. Phys. (2006), 207:554-562.
Wei; et al., "Melting and Crystallization Behaviors of Biodegradable Polymers Enzymatically Coalesced from Their Cyclodextrin Inclusion Complexes", Biomacromolecules (2003), 4:783-792.
Xu; et al., "Improvements of thermal property and crystallization behavior of PLLA based multiblock copolymer by forming stereocomplex with PDLA oligomer", Polymer (2006), 47:3922-3928.
Yang; et al., "Miscibility and Crystallization of Poly(L-lactide)/Poly(ethyleneglycol) and Poly(L-lactide)/Poly(s-caprolactone) Blends", Polymer Journal (1997) 29(8):657-662.
Yavuz; et al., "Preparation and degradation ofl-lactide and s-caprolactone homo and copolymer films", Polymer Degradation and Stability (2002), 75:431-437.
Dirk Wybe Grijpma, High Impact Strength Poly(Lactide) Tough Biodegradable Materials (Oct. 1, 1993) (Thesis, University of Groningen).

* cited by examiner

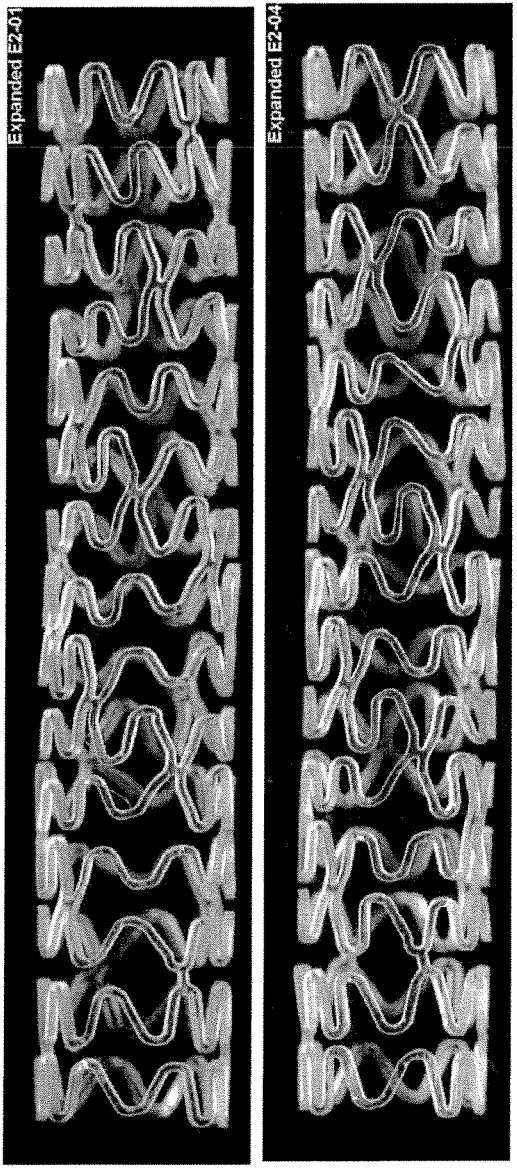
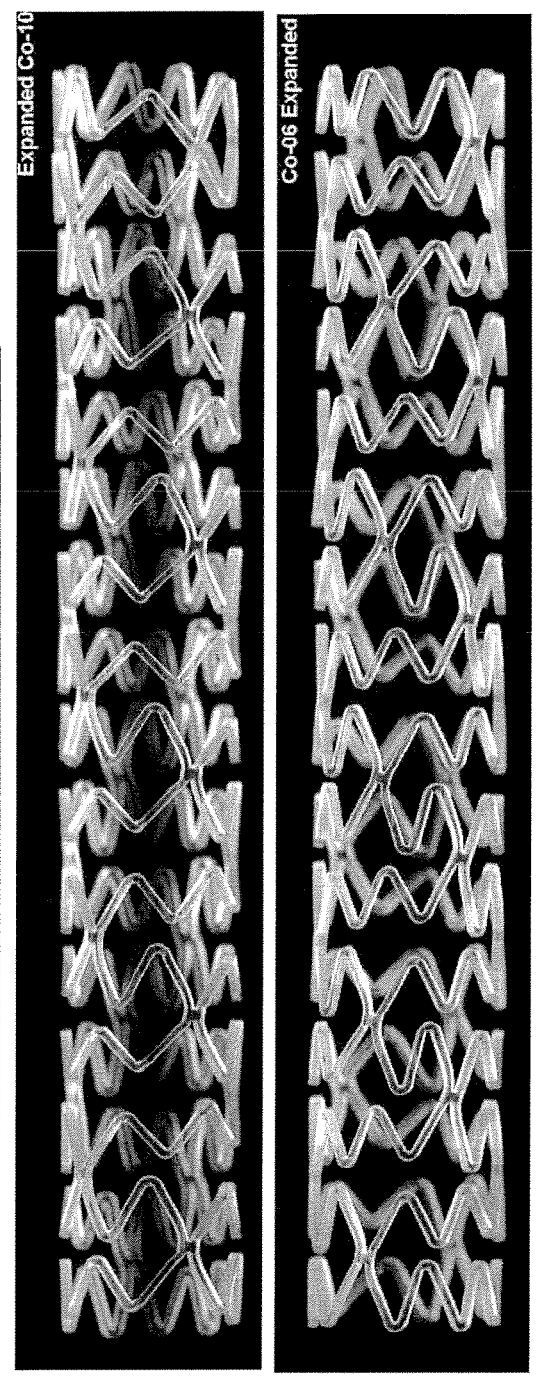
PLLA E2 R-Stent
FIG. 3A
PLLA CoCr R-Stent
FIG. 3B

BIOABSORBABLE POLYMERIC COMPOSITION AND MEDICAL DEVICE

CROSS-REFERENCE TO RELATED APPLICATIONS

This application is a continuation of U.S. application Ser. No. 11/875,892, filed Oct. 20, 2007, now U.S. Pat. No. 8,691,321, which claims priority from U.S. Provisional Application No. 60/862,433, filed Oct. 20, 2006, the disclosure of each of which is incorporated by reference herein in its entirety.

BACKGROUND

All references cited in this specification, and their references, are incorporated by reference herein in their entirety where appropriate for teachings of additional or alternative details, features, and/or technical background.

The invention relates to a medical device for implantation into vessels or luminal structures within the body. In one embodiment, the present invention relates to stents and synthetic grafts which are coated with a controlled-release matrix comprising a medicinal substance for direct delivery to the surrounding tissues, which may include a ligand attached thereto for capturing progenitor endothelial cells in the blood contacting surface of the device to form mature, functional, endothelium at site of injury. In particular, the polymer matrix/drug/ligand-coated devices such as stents are for use, for example, in therapy of diseases and conditions such as restenosis, artherosclerosis, and endoluminal reconstructive therapies.

Disclosed in embodiments herein is a novel tube-shaped expandable scaffold configured to fit within the vasculature, including the cardiovasculature, having a low, propensity for biological rejection. Such scaffold may consist of, or comprise, a bioabsorbable polymer composition or blend that effectuates a combination of mechanical properties balancing elasticity, rigidity and flexibility. The polymer composition may include a base material including a bioabsorbable polymer, copolymer, or terpolymer, and a copolymer or terpolymer additive. Advantageously the polymer may be selected to undergo enzymatic degradation and absorption. In particular, the composition may allow for a "soft" breakdown mechanism allowing for the breakdown of the component polymers to be less injurious to the surrounding tissue.

A persistent problem associated with the use of metallic devices such as stents is found in the formation of scar tissue coating of the vascularly located stent, the so-called process of restenosis. Many have concluded that the continued risk of stent thrombosis due to the permanent aspect of metal stents has not been overcome by coating of the metal with drugs intended to prevent such calamities. On the contrary, an increase in death rate has also been associated with a number of these coatings. Moreover, metallic and polymeric stents may prevent vascular lumen remodeling and expansion.

With respect to stents, stents may prevent the healing of tissue and reduce complement activation of the immune response. Stents have also been associated in some instances with a reduced inflammatory response and trauma upon break-up of an implant and/or its component materials. Conventional stents may also not provide a desired degree of flexibility in shape allowing for easier implantation, particularly into blood vessels.

The present inventors have recognized a need to develop medical devices such as stents and vascular synthetic grafts, manufactured from biocompatible, biodegradable bioabsorbable polymer blends as base polymer which are useful for the treatment of disease, in particular of the vascular system. The medical devices may ameliorate problems associated with present devices.

As disclosed herein, it has been recognized by the present inventors that the base polymer may be selected to allow additional molecular free volume to encourage sufficient molecular motion so as to allow for re-crystallization to occur at physiological conditions (e.g., upon the addition of molecular strain). Increased molecular free volume may allow for an increase in the rate of water uptake adding both a plasticizing effect as well as increasing the bulk degradation kinetics.

In embodiments herewith, the compositions allow for a "soft" breakdown mechanism such that the breakdown proceeds while being friendly to the surrounding tissue (less inflammatory response, and rendering lower potential for trauma upon break up of an implant). By selecting a polymer or copolymer having an enhanced hydrophilic property for either the base or the additive or both, the polymer blend may reduce complement activation and minimize or prevent opsonization.

In certain embodiments, the bioabsorbable scaffolds allow flexibility and stretchability suitable for the implantation in the pulse movements, contractions and relaxations of, for example, the cardiovascular system.

REFERENCES

Reference is made to U.S. Pat. No. 6,607,548 B2 (Inion), issued Aug. 19, 2003, which discloses biocompatible and bioresorbable compositions comprising a lactic acid or glycolic acid based polymer or copolymer blended with one or more copolymer additives. Such implants are asserted to be cold-bendable without crazing or cracking. Reference is also made to EP 0401844, which discloses a blend of poly-L-lactide with poly D-DL-lactide, and U.S. Pat. No. 6,001,395 which discloses drug delivery with lamellar particles of a biodegradable poly(L-lactide) or copolymers or blends thereof, being at least in part crystalline. U.S. Pat. No. 7,070,607 discloses an aneurysm repair coil comprising a bioabsorbable polymeric material carrying an embolic agent wherein the thrombogenicity is controlled by the polymer composition.

SUMMARY

Embodiments disclosed herein are method of manufacturing bioabsorbable medical devices, such as stents and synthetic grafts comprising a bioabsorbable polymer composition. The medical devices are biocompatible, biodegradable and can deliver mechanical support as well as pharmaceutical substances to an injured organ after implantation into a patient.

In one embodiment, the medical devices are configured to encapsulate therapeutic agents within the walls of their structure for the treatment of diseases such as artherosclerosis, restenosis and the like. In one embodiment, as the bioabsorbable device breaks down, the device provides controlled released of the pharmaceutical trapped within its wall or integrally part of the polymeric composition. In this and other embodiments, pharmaceutical substances can be covalently attached or admixed to the polymeric material comprising the medical device. In certain embodiments, the medical device may have a coating for stimulating restoration of normal endothelium at the site of implant.

In one embodiment, there is provided a method for the manufacturing of a polymeric medical device with a coating. The method comprises the making of a polymeric medical device from a bioabsorbable polymeric composition comprising a base polymer which can be a crystallizable polymer. The method comprises making a crystallizable polymeric composition; forming a structure such as a structure which is the form of a medical device, for example, a stent; coating said structure in its luminal surface with one or more layers of a composition comprising a polymeric matrix and with or without one or more pharmaceutical substance and a ligand for recognizing and binding to target cells in the circulation. The method further comprises the step of coating the medical structure in an opposing surface, in the case of a stent, coating the abluminal surface with a composition comprising the same or different pharmaceutical substance for local delivery to the surrounding tissue.

In one embodiment, the method of manufacturing further comprises the step of designing and cutting the polymer device to a specific structure prior to coating the device or after coating the device. In this embodiment, the pharmaceutical substance and compositions comprising the coating can be applied prior to designing and cutting the device structure, or after the device is coated.

In one embodiment, there is disclosed a cardiovascular tube-shaped expandable scaffold such as a stent, fabricated from a bioabsorbable polymer composition or blend having a combination of mechanical properties balancing elasticity, rigidity and flexibility allowing bending and crimping of the scaffold tube onto an expandable delivery system (such as a balloon catheter) which is attached to a suitable vascular lumen insertion means. The deployed scaffold may be expanded from a narrowly crimped delivery conformation to a lumen diameter sufficient for implantation onto the vascular wall tissue. The flexible form of a polymer scaffold may also afford the capability of overstretching its configuration so as to facilitate insertion into blood vessel with minimal vessel wall contact. In addition, the scaffold can be manipulated to vary from a cylindrical to a truncated conical shape allowing for easy implant installation, relocation, and adjustment.

In one embodiment, the medical device is provided in an expandable scaffold, which provides a crimpable and expandable structure without stress crazing. In embodiments wherein the medical device is a stent, the expandable scaffold provides a set of interlocking struts for stabilizing the device in its deployed or expanded or implanted conformation.

Another embodiment of the scaffold polymer provides enhanced mechanical properties through a molecular reorientation and crystallization during the radial strain of expansion from a crimpable state to an expanded state.

In one embodiment, the medical device is provided as a scaffold implant in a delivery system comprising a catheter adapted with a balloon type reversible inflation or dilation means. In one embodiment, a balloon inflating device may be employed which may be heated or cooled.

In an alternate embodiment, the medical device is provided with a polymer breakdown moieties that are "friendly" at the contact vascular wall area. In certain embodiments, the breakdown kinetics are sufficiently slow to avoid tissue overload or other inflammatory reactions.

In one embodiment there is provided a minimum of 30-day retention of clinically supportive strength that may endure in place, for example, about 3-4 months. Evaluation criteria for such embodiment scaffolds may be based, for example, on mass loss in terms of decreased molecular weight, retention of mechanical properties, and tissue reaction.

In alternate embodiments, the medical device comprising a expandable scaffold is operably configured to change to from a solid state to a "rubbery state," allowing for easier surgical intervention. In this embodiment, the rubbery state of the device is attained one the device is in physiological conditions in vivo.

Optionally the polymers and construction of the device may be selected to have flexibility and elasticity suitable for an implant in friction-free contact with vascular walls during the cardiovascular pulsing contractions and relaxations.

Preferably the scaffold in an embodiment is stretchable and elastic but has a sufficiently rigid strength to be capable of withstanding the cardiovascular fluctuating pressures within a blood vessel.

According to an embodiment, the bioabsorbable polymer is composed of a poly(L-lactide) or a poly(D-lactide) base polymer. Modifying copolymers include poly L (or D)-lactide-co-Tri-methylene-carbonate or poly-L (or D)-lactide-co-e-caprolactone may be used to link the base polymers. These copolymers can be synthesized as block copolymers or as "blocky" random copolymers wherein the lactide chain length is sufficiently long enough to crystallize. The development of a crystalline morphology may enhance the mechanical properties of the medical device; enhance processing conditions, and provide the potential of cross-moiety crystallization, for example, thermal cross-links. In this embodiment, the polymer composition allows the development of the lactide racemate crystal structure, between the L and D moieties, to further enhance the mechanical properties of the medical device.

It is also envisioned that the degradation time of the polymer in the composition may be shortened by enhancing degradation kinetics. For example, the starting material may be a lower molecular weight composition and/or a base polymer may be employed that is more hydrophilic or liable to hydrolytic chain scission.

According to embodiments of the invention there is provided a compositions and methods for fabricating a base copolymer having one moiety, such as L-lactide or D-lactide, is sufficiently long enough and not sterically hindered to crystallize, with a lesser moiety, for example Glycolide or Polyethylene Glycol (PEG) or monomethoxy-terminated PEG (PEG-MME).

The compositions, in addition to the base polymer, the modifying polymer or co-polymer, may include other materials and compounds that enhance degradation kinetics such as e-caprolactone copolymer moiety, wherein the caprolactone remains amorphous with resulting segments more susceptible to hydrolysis. Such compositions may be manufactured, for example, by admixing with the base polymer blend, or reacting to the base polymer.

The composition may incorporate PEG copolymers, for example either AB diblock or ABA triblock with the PEG moiety being approximately 1%. The mechanical properties of the lactide (see Enderlie and Buchholz SFB May 2006) may be maintained. The incorporation of either PEG or PEG-MME copolymers may also be used to facilitate drug attachment to the polymer, for example in conjunction with a drug eluting medical device.

Another embodiment provides a scaffold base polymer combining polymers of low PEG content of less than 5% in high MW, i.e., 2-3 IV copolymers, which enables the lactide block to crystallize and impart equivalent strength to the base polymer.

The scaffold of embodiments herein may provide a polymer core material containing at least one encapsulated drug for localized treatment of the vascular wall and lumen. The scaffold core degradation schedule may provide, for example, a simultaneously slow release of medication for the treatment and prevention of tissue inflammation and platelet aggregation.

Another embodiment of the polymer composition or blend provides uniform degradation in situ avoiding polymer release in chunks. The scaffold may carry at least one attached or embedded identification marker made from a radioopaque material.

BRIEF DESCRIPTION OF THE DRAWINGS

FIG. 3A and FIG. 3B are photographs of bioabsorbable stents comprising poly(L-Lactic) acid.

DETAILED DESCRIPTION

Figure 1:
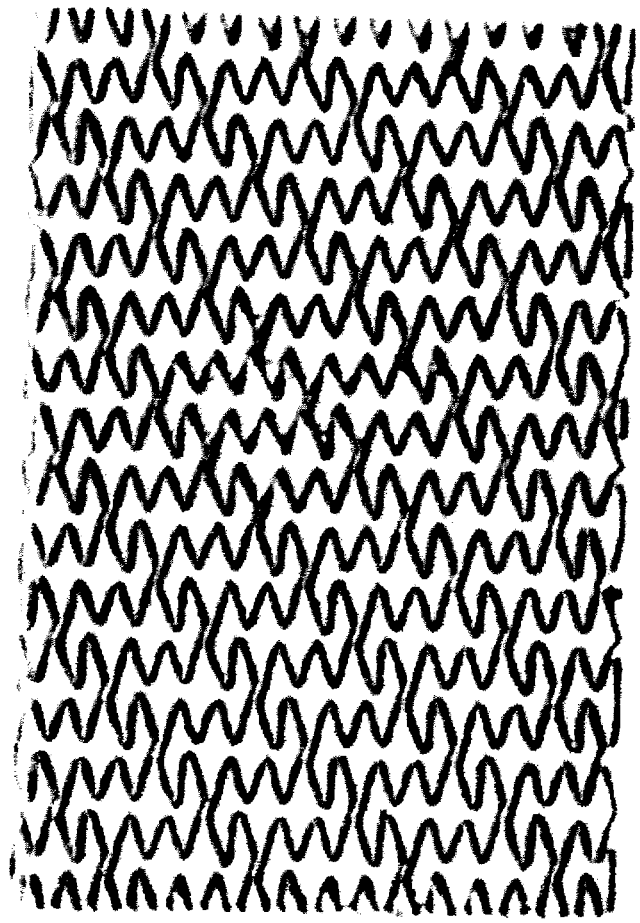
FIG. 1 illustrates a representative bioabsorbable stent design.
Figure 2:
FIG. 2 is a photograph of a representative bioabsorbable stent device.
Figure 4A:
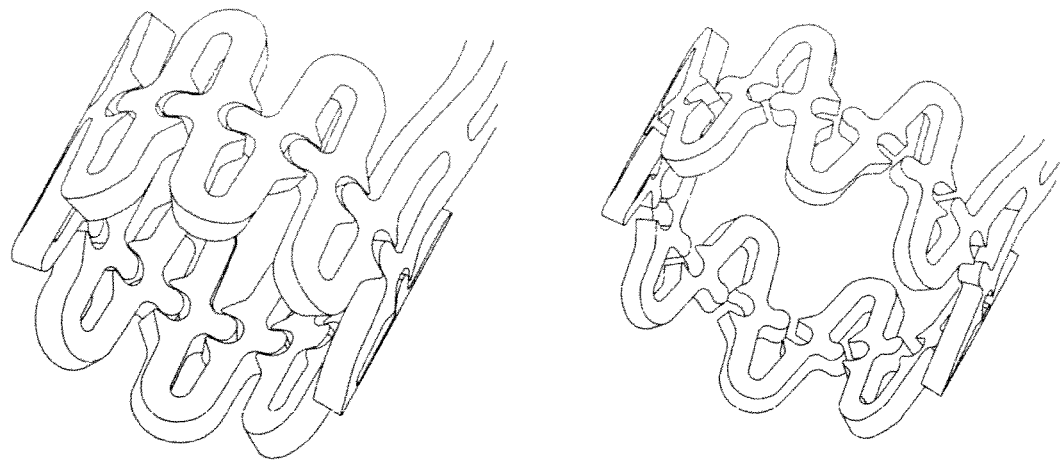
FIG. 4A illustrates a bioabsorbable stent design comprising stabilizing interlocking mechanism.
Figure 4B:
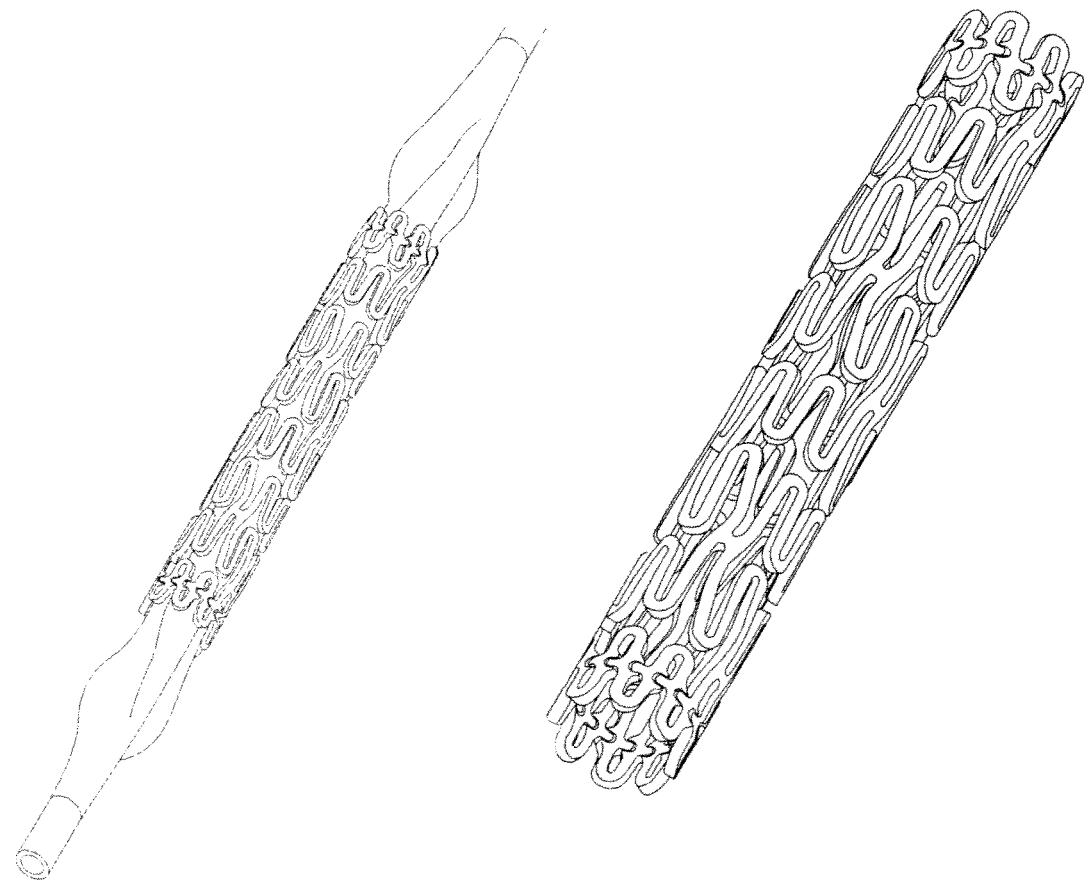
FIG. 4B illustrate a bioabsorbable stent design mounted on a balloon catheter and also showing the interlocking mechanisms at the free ends.
Figure 5A:
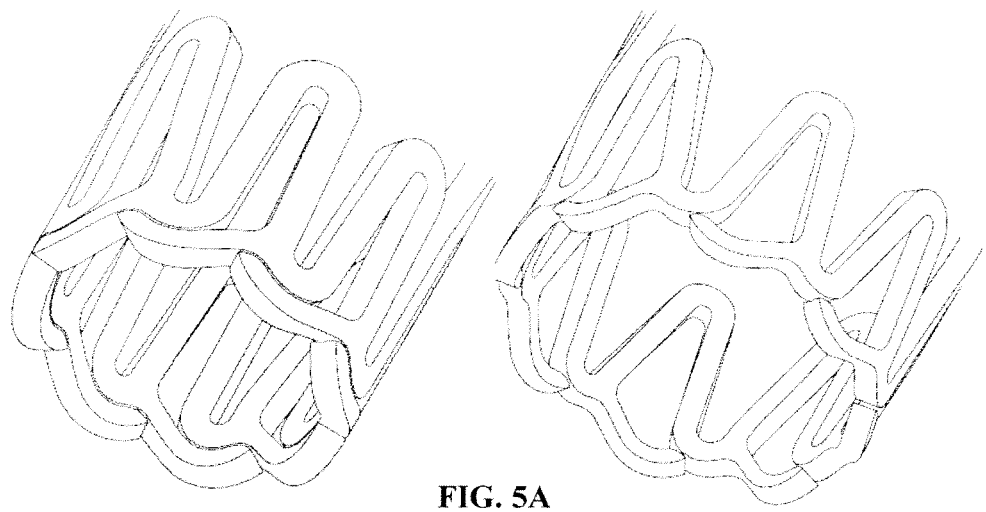
FIG. 5A and FIG. 5B illustrate a bioabsorbable stent design comprising stabilizing interlocking mechanism at the ends.
Figure 5B:
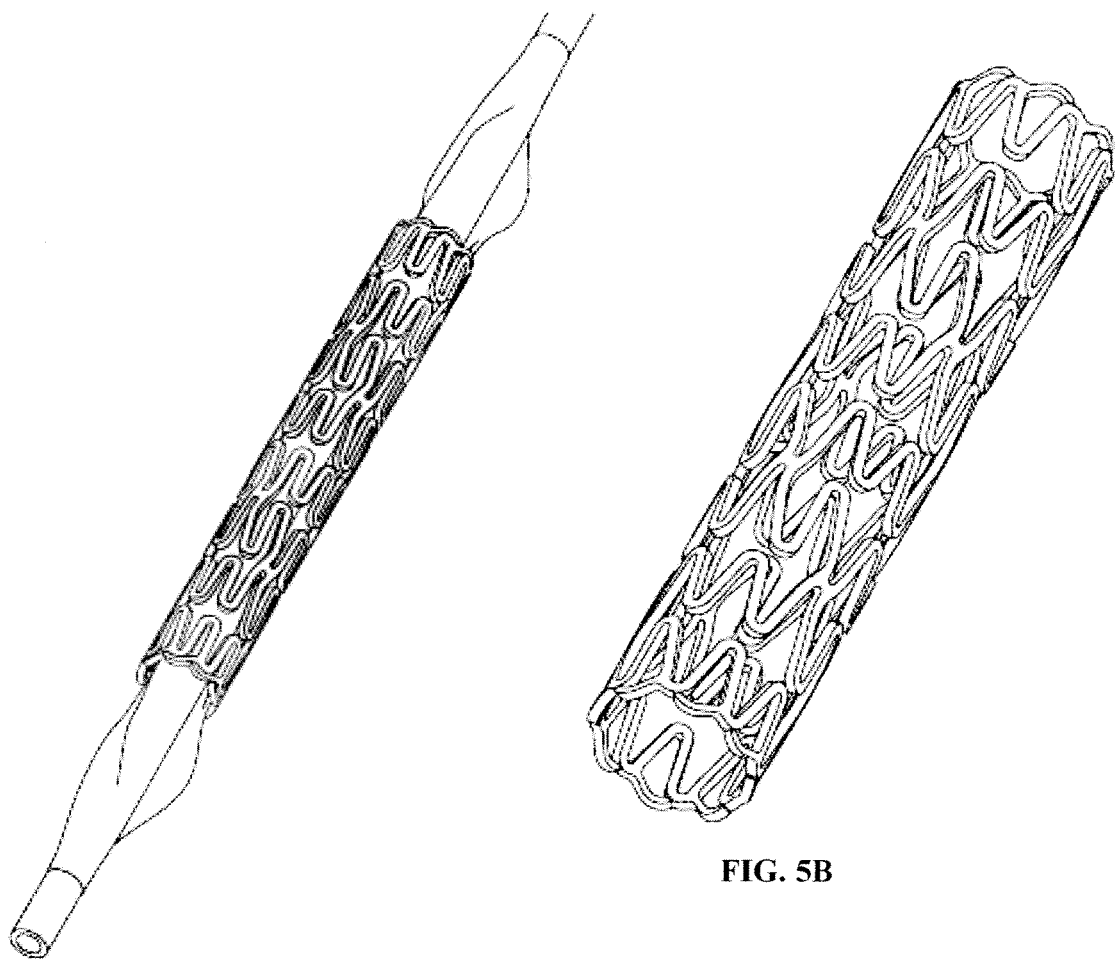
Figure 6:
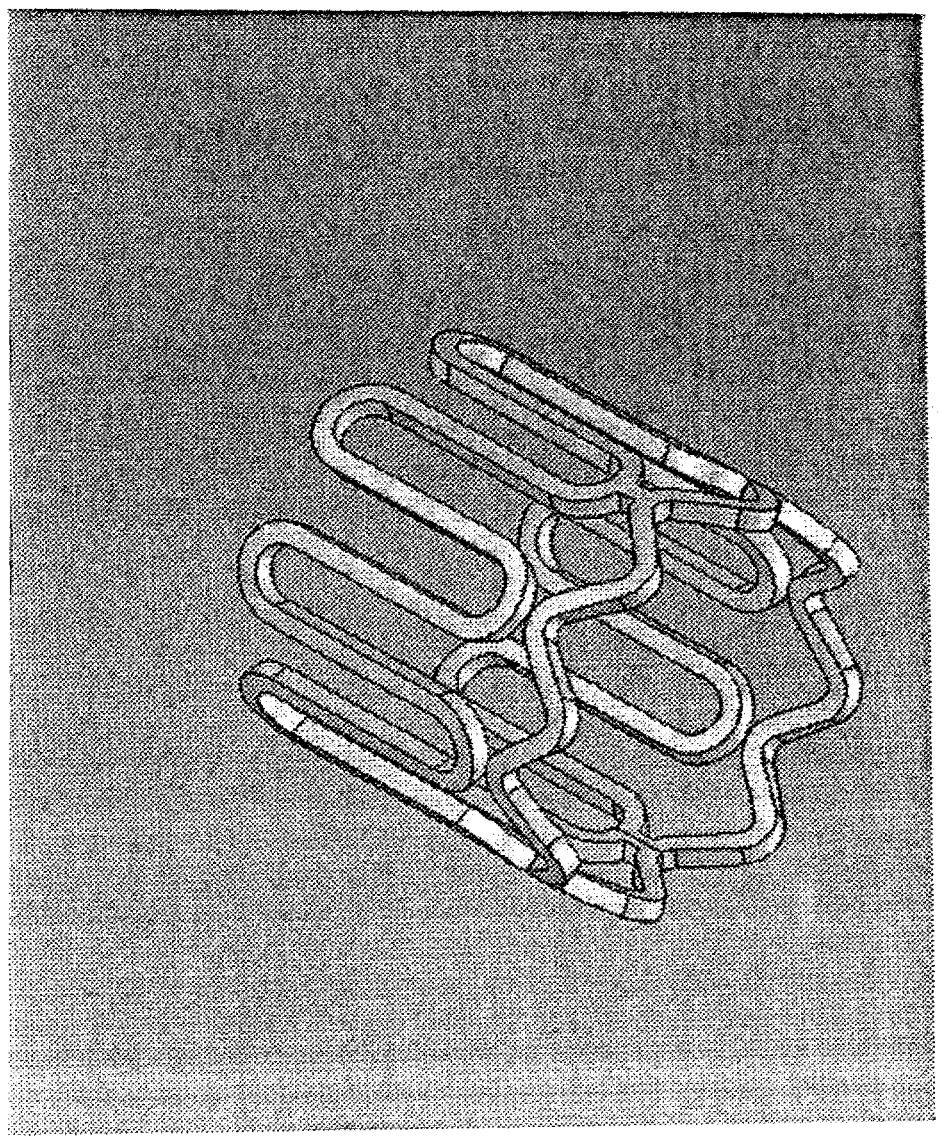
FIG. 6 illustrates a bioabsorbable stent design depicting a folded ring segment.
Figure 7:
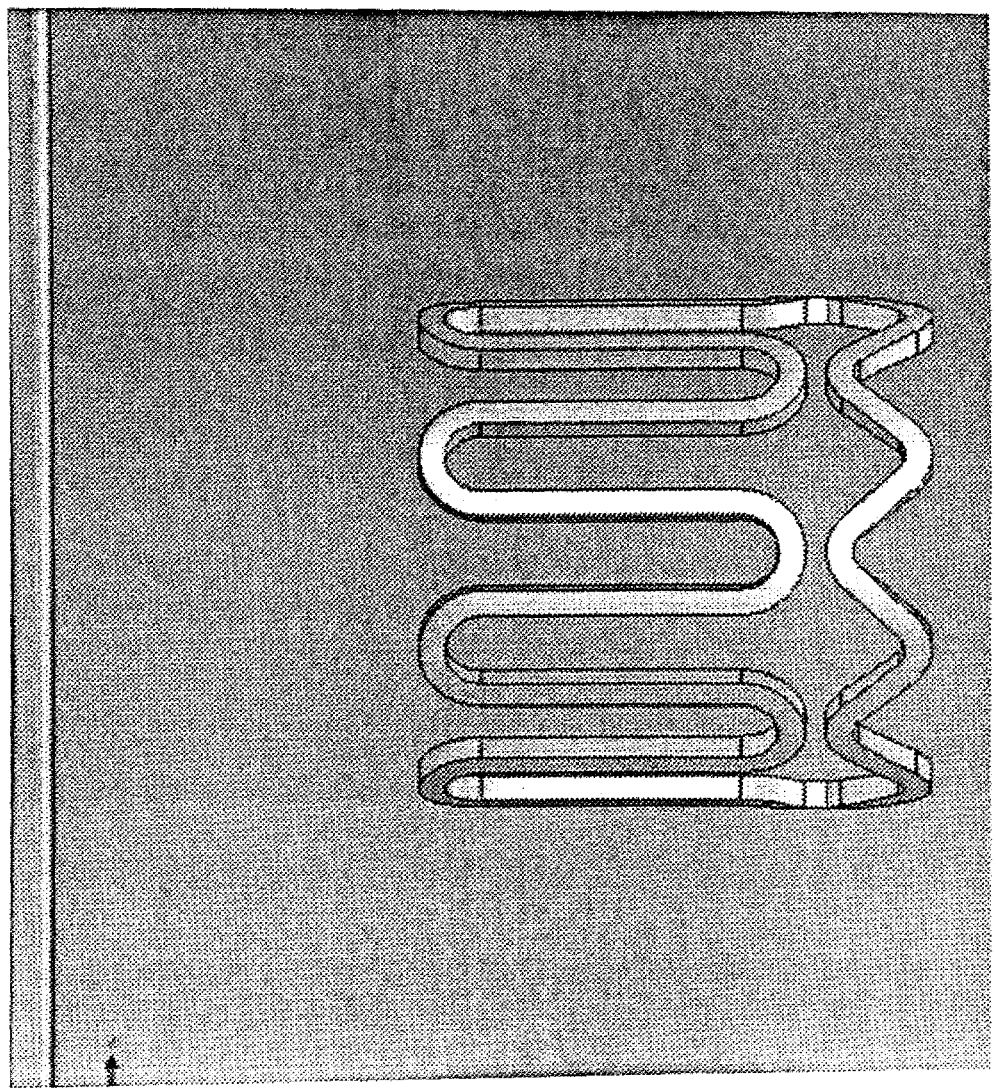
FIG. 7 illustrates a bioabsorbable stent design depicting a ring segment.
Figure 8:
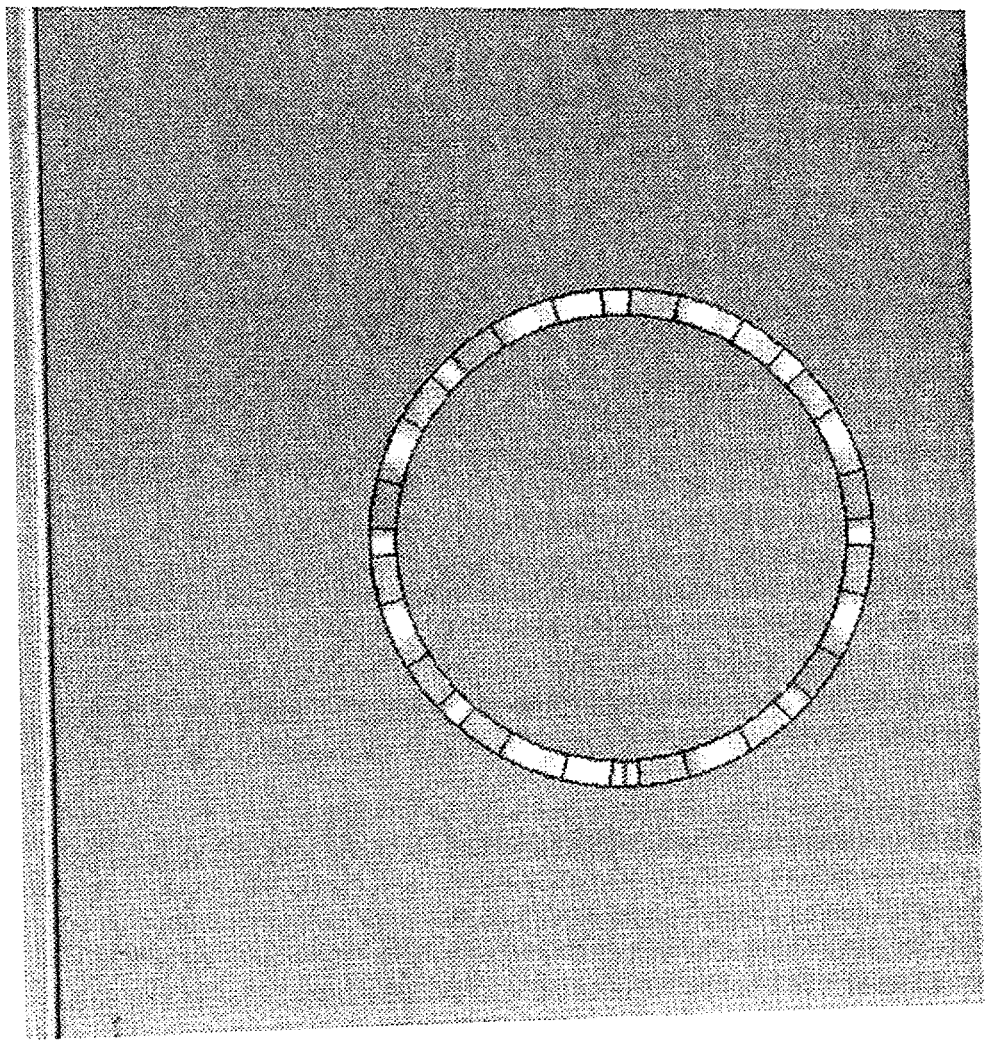
FIG. 8 illustrates a bioabsorbable stent design depicting a fully expanded diameter.
Figure 9B:
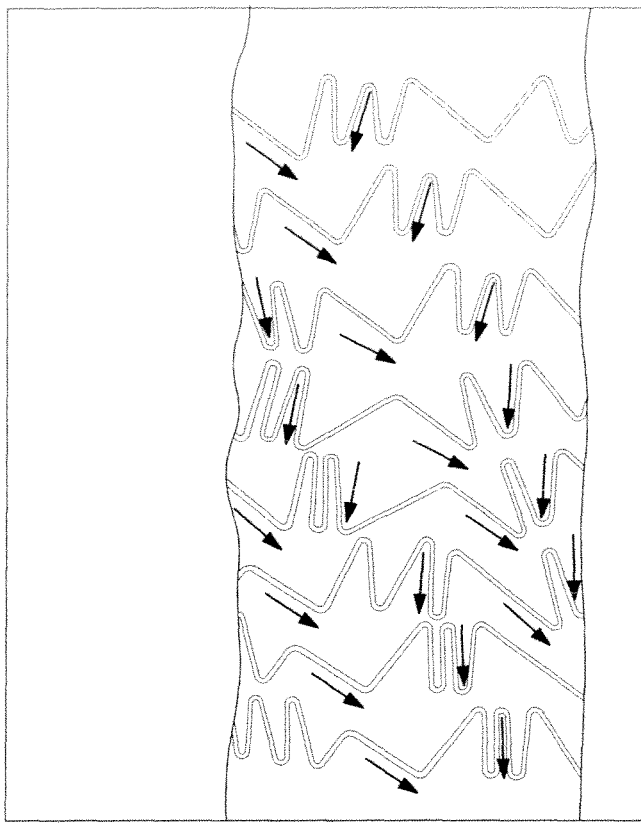
FIG. 9A and FIG. 9B illustrate a bioabsorbable stent struts design depicting a the direction of stress points on the components of the scaffold.
Figure 9A:
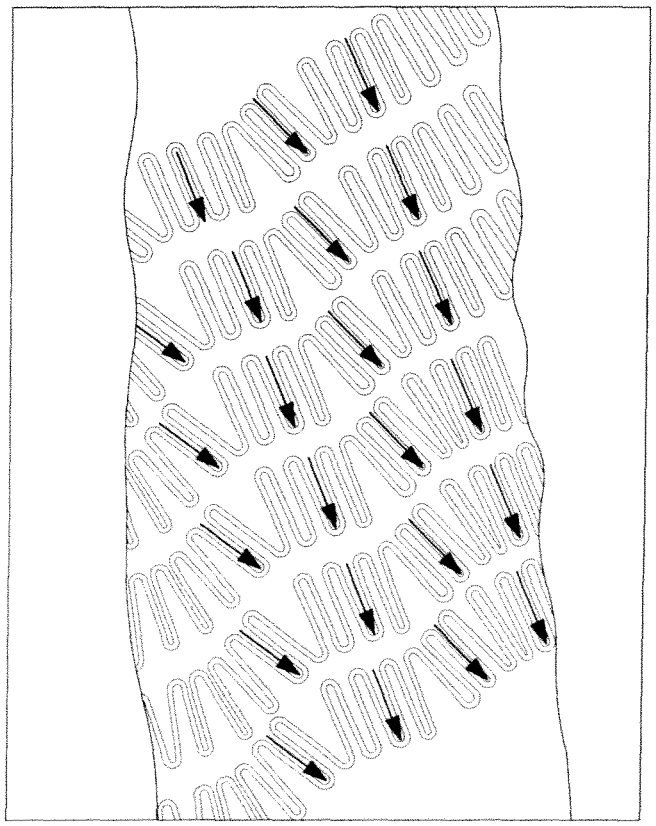
Figure 10A:
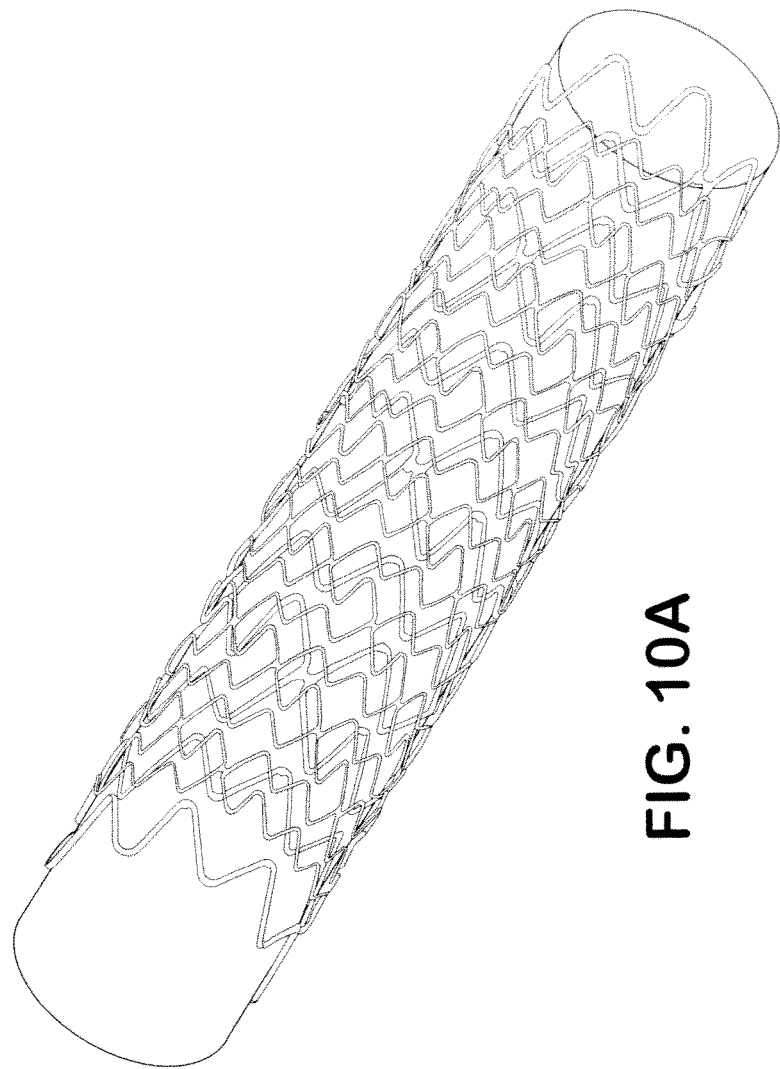
FIG. 10A and FIG. 10B illustrate an embodiment of a bioabsorbable stent design.
Figure 10B:
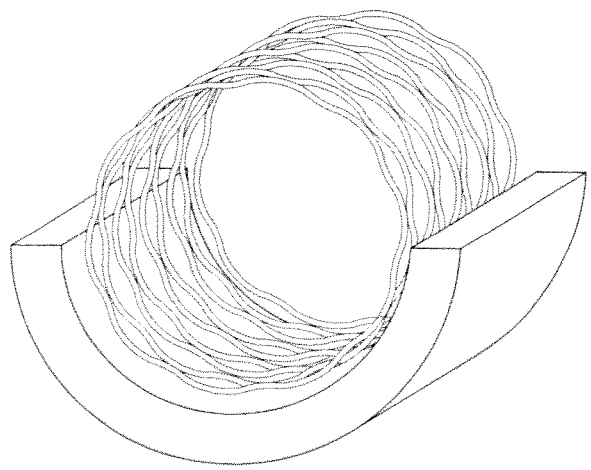

Polymer compositions of the present invention may be used to manufacture medical device for implantation into a patient. The medical devices are scaffolds having biodegradable, bioabsorbable properties and include, but are not limited to, stents, stent grafts, vascular synthetic grafts, catheters, shunts, vascular shunts, valves, grafts and the like.

The invention is also directed to methods of making the biodegradable polymer compositions and methods for making the medical devices from the polymer compositions disclosed herein.

In one embodiment, the medical device comprises a crimpable polymeric stent, which can be inserted onto a balloon delivery system for implantation. The balloon may comprise a thermal balloon or non-thermal balloon. The medical device can have a structure which is crimpable during loading and expandable without stress under physiological conditions. The medical device may comprise a structure that comprises polymers that which can orient and/or crystallize upon strain of deployment, for example during balloon dilation, in order to improve the medical devices mechanical properties. By employing a medical device comprising polymers having slow breakdown kinetics one may avoid tissue overload or other inflammatory responses at the site of implantation.

The medical devices of the invention, can be structurally configured to provide the ability to change and conform to the area of implantation and to allow for the normal reestablishment of local tissues. The medical devices can transition from solid to a "rubbery state" allowing for easier surgical intervention, than, for example a stainless steel stent. A medical device may be designed to have, for example, a minimum of 30-day retention of clinically sufficient strength.

In one embodiment, the medical device is comprised of a polymer composition can comprise a base polymer which can be present from about 60% to about 95% by weight, or from about 70% to about 80% by weight of the composition. For example, the polymer formulation can comprise from about 70% by weight poly L-lactide (about 1.5 to 3.5 or from about 2.5 to 3 IV) with the poly L-lactide-co-TMC (80/20 w/w) (1.0 to 2.6 IV or from about 1.4 to 1.6 IV).

In another embodiment, the polymer formulation comprises 70% by weight triblock poly L-lactide-co-PEG (95/5 to 99/01, or from about 98/2 to 99/01) (2,000 to 100 Mw PEG, or 6,000 to 8000 Mw PEG) with the poly L-lactide-co-TMC (70/30) (1.4 to 1.6 IV). The polymer composition may also comprise a formulation of about 70% by weight diblock poly L-lactide-co-PEG-MME (95/05 to 99/01) (2,000 to 100 Mw PEG-MME, or 6,000 to 8000 Mw PEG-MME) with poly L-lactide-co-TMC (70/30 w/w) (1.4 to 1.6 IV).

Pharmaceutical compositions may be incorporated with the polymers by for example grafting to the polymer active sites, impregnating or encapsulating within the polymer composition prior to forming the medical device so as to integrate the composition within the walls of the device and/or coating the medical device one formed on the surface of the device, in particular the abluminal surface.

In embodiments disclosed herein, the medical device comprises a stent, which is structurally configured to be deployed into, for example, an artery or a vein, and be able to expand in situ, and conform to the blood vessel lumen the stent may be used to reestablish blood vessel continuity at the site of injury. The stent can be configured to have many different arrangements so that it is crimpable when loading, and expandable and flexible at physiological conditions once deployed. The biodegradable medical device may comprise a base polymer comprising, for example ply L-Lactide or poly D-Lactide, modifying co-polymer(s), such as poly L (or D) lactide-co-Tri-methylene-carbonate or poly L (or D)-lactide-co-e-caprolactone, as described above.

Figure 11A:
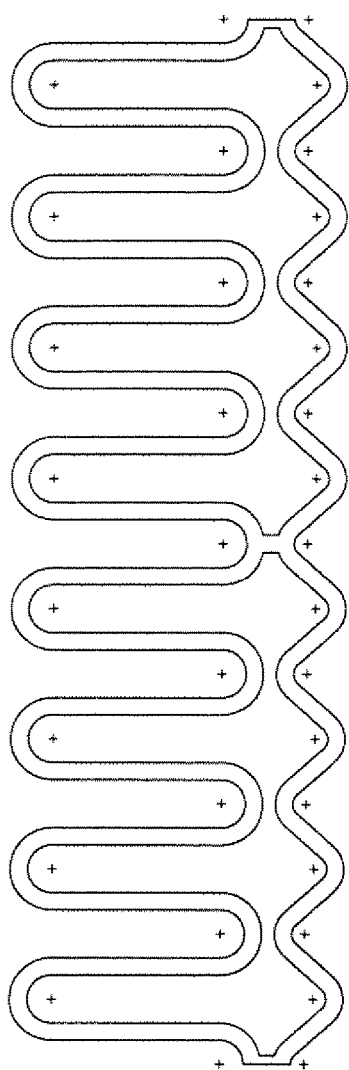
FIG. 11A illustrates a bioabsorbable stent design depicting a folded ring segment and the ring segment in its open configuration.
Figure 11A:
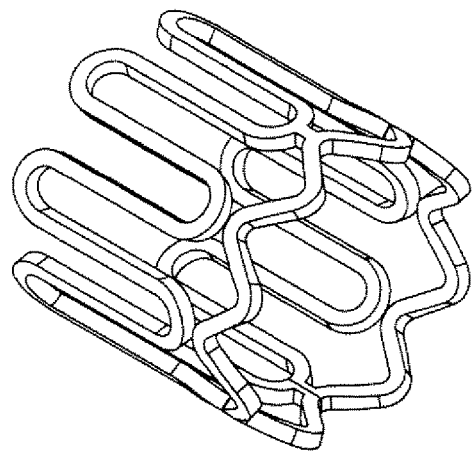
Figure 11B:
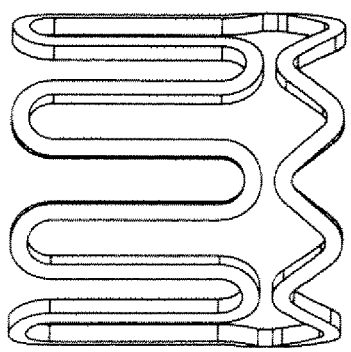
FIG. 11B shows the stent design from an alternate angle.
Figure 11B:
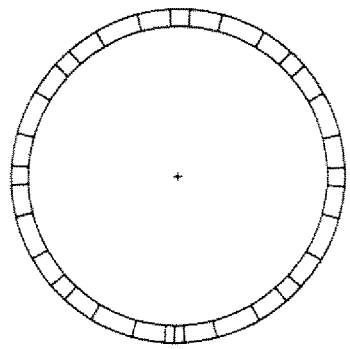
Figure 12A:
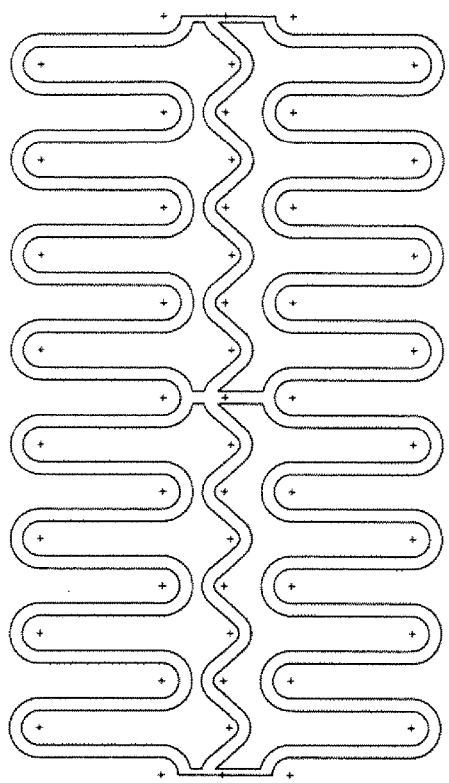
FIG. 12A and FIG. 12B illustrate an alternate bioabsorbable stent design depicting a ring segment in different states.
Figure 12A:
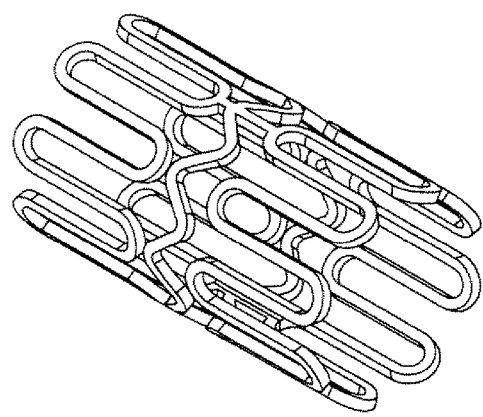
Figure 12B:
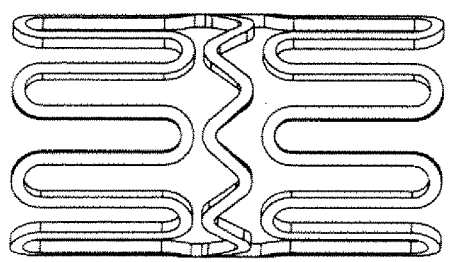
Figure 12B:
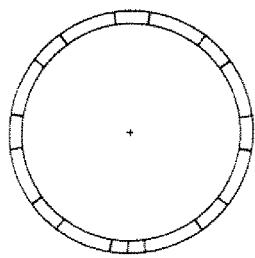
Figure 13:
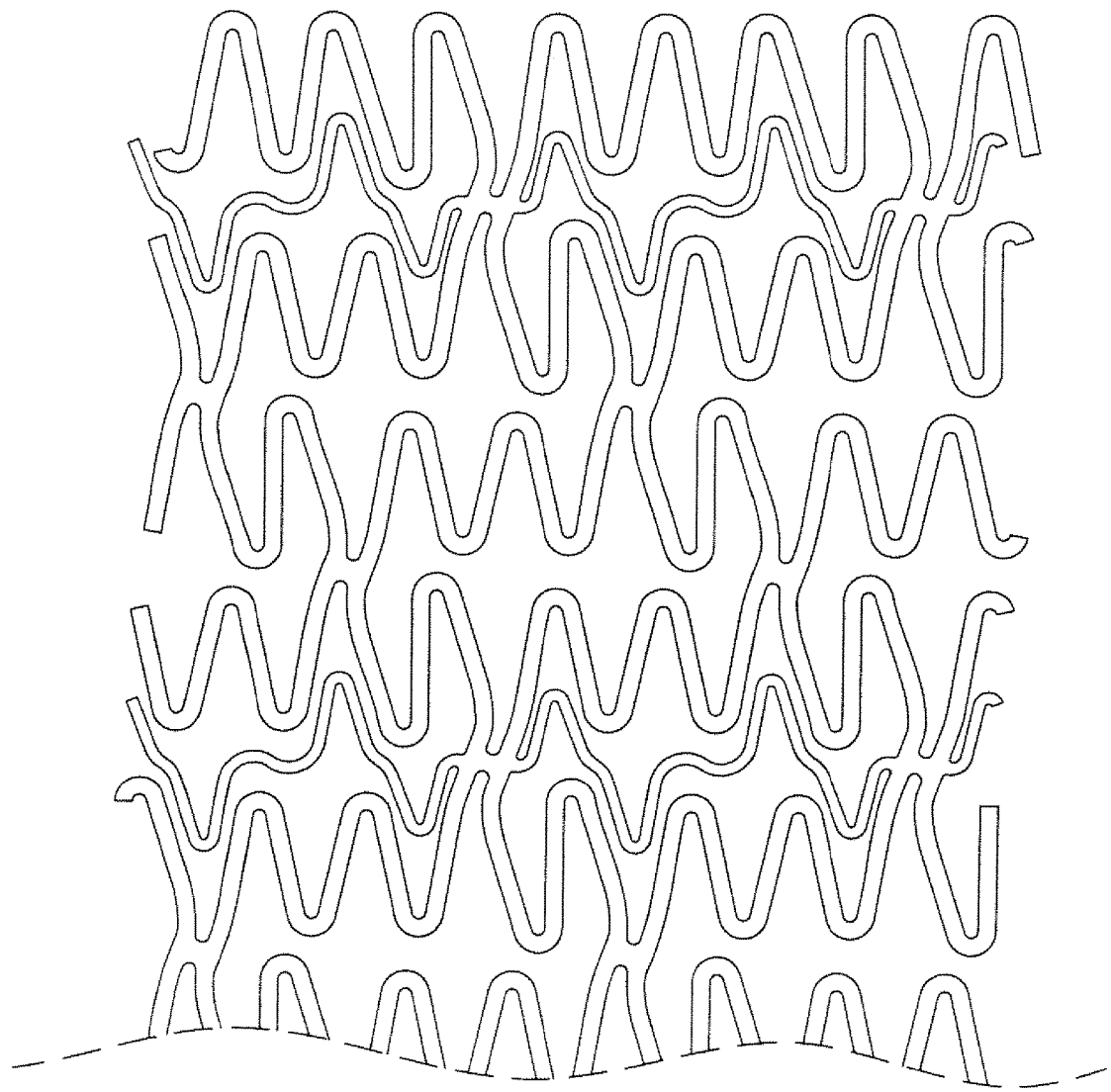
FIG. 13 and FIG. 14 illustrate bioabsorbable stent designs depicting the configuration of the wall of a stent and its segments.
Figure 14:
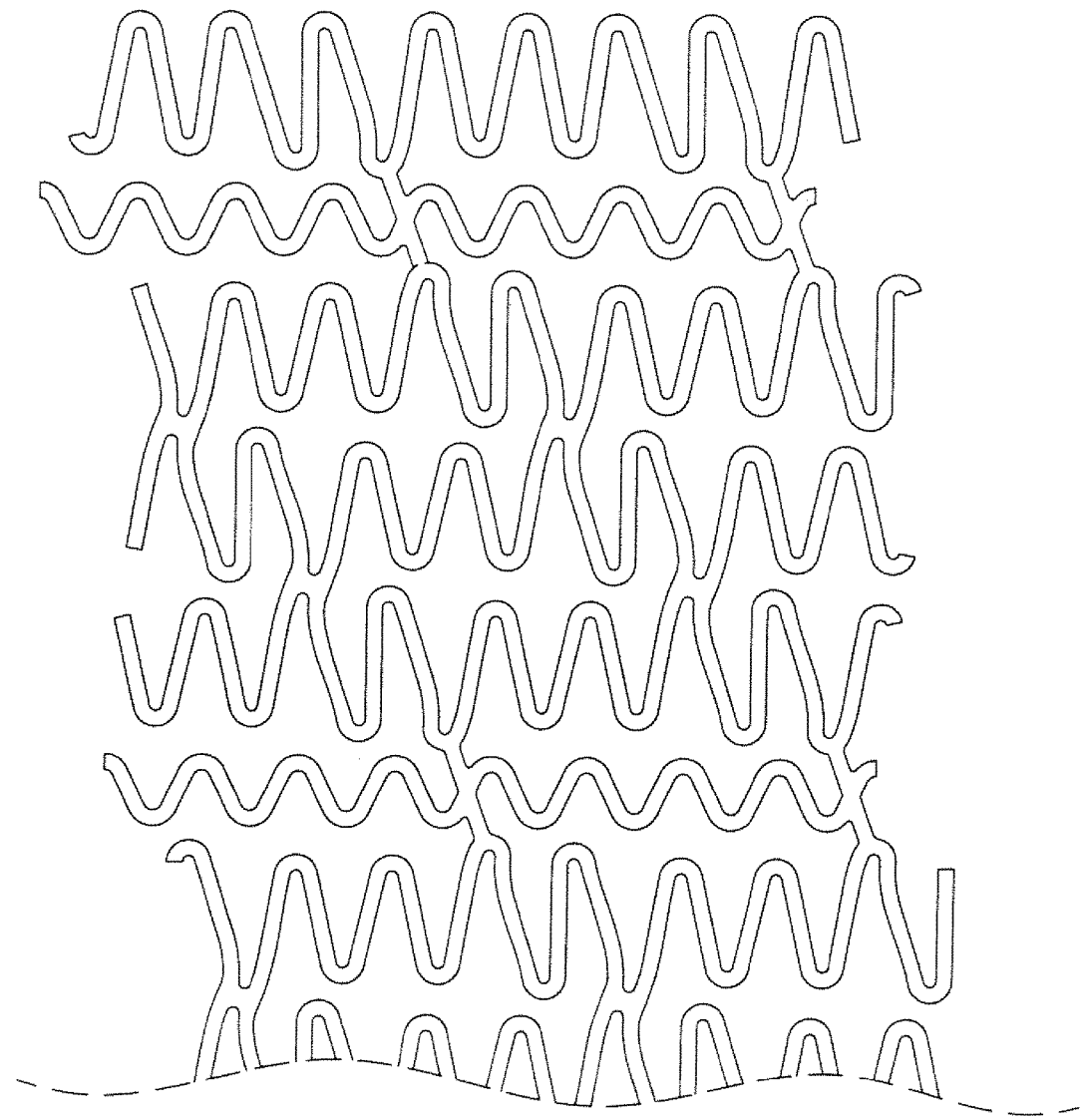
Figure 15:
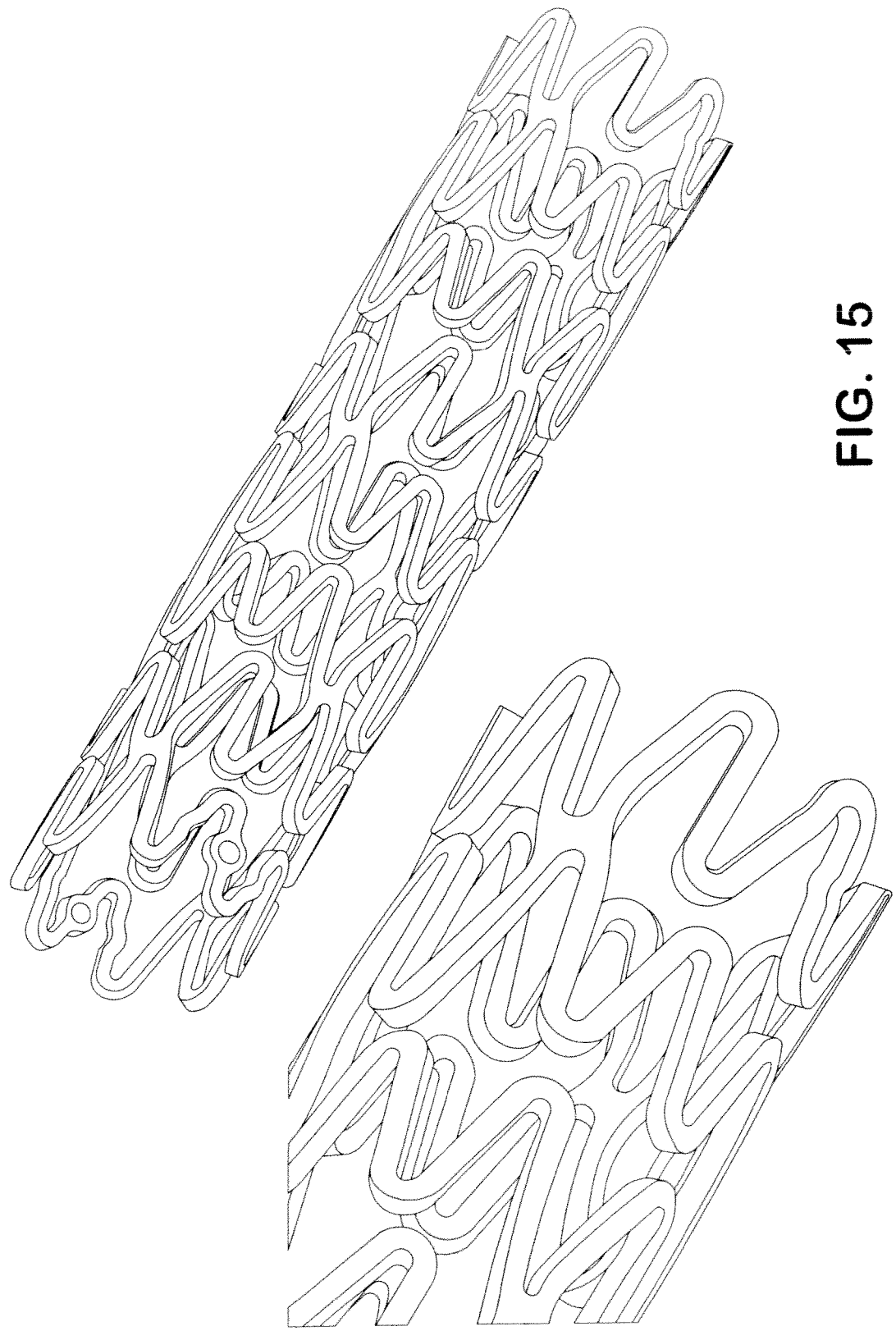
FIG. 15 illustrates a bioabsorbable stent design comprising a radiopaque marker integrated within the stent wall.
Figure 16:
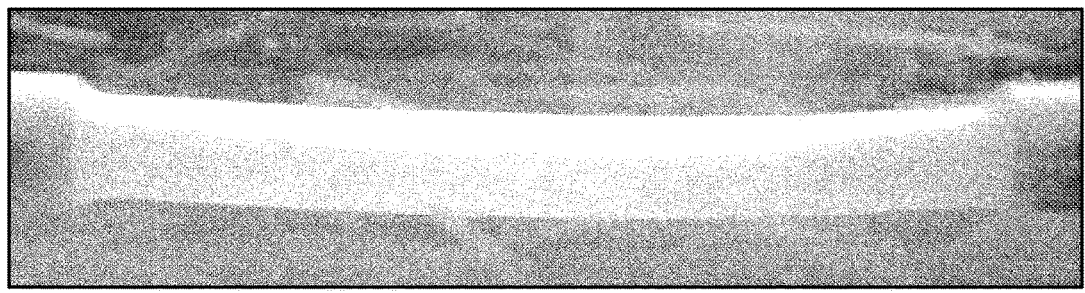
FIG. 16 illustrates a bioabsorbable stent design depicting a the average body collapse pressure. (Average body collapse pressure: (1) PLLA E2 R-stent (n=3): 4.5 psi (SD 0.3 psi); (2) PLLA CoCr R-stent (n=3): 2.7 psi (SD 0.4 psi). Upon removal of pressure, all crushed stents recovered 40+% of lumen diameter.)
Figure 17:
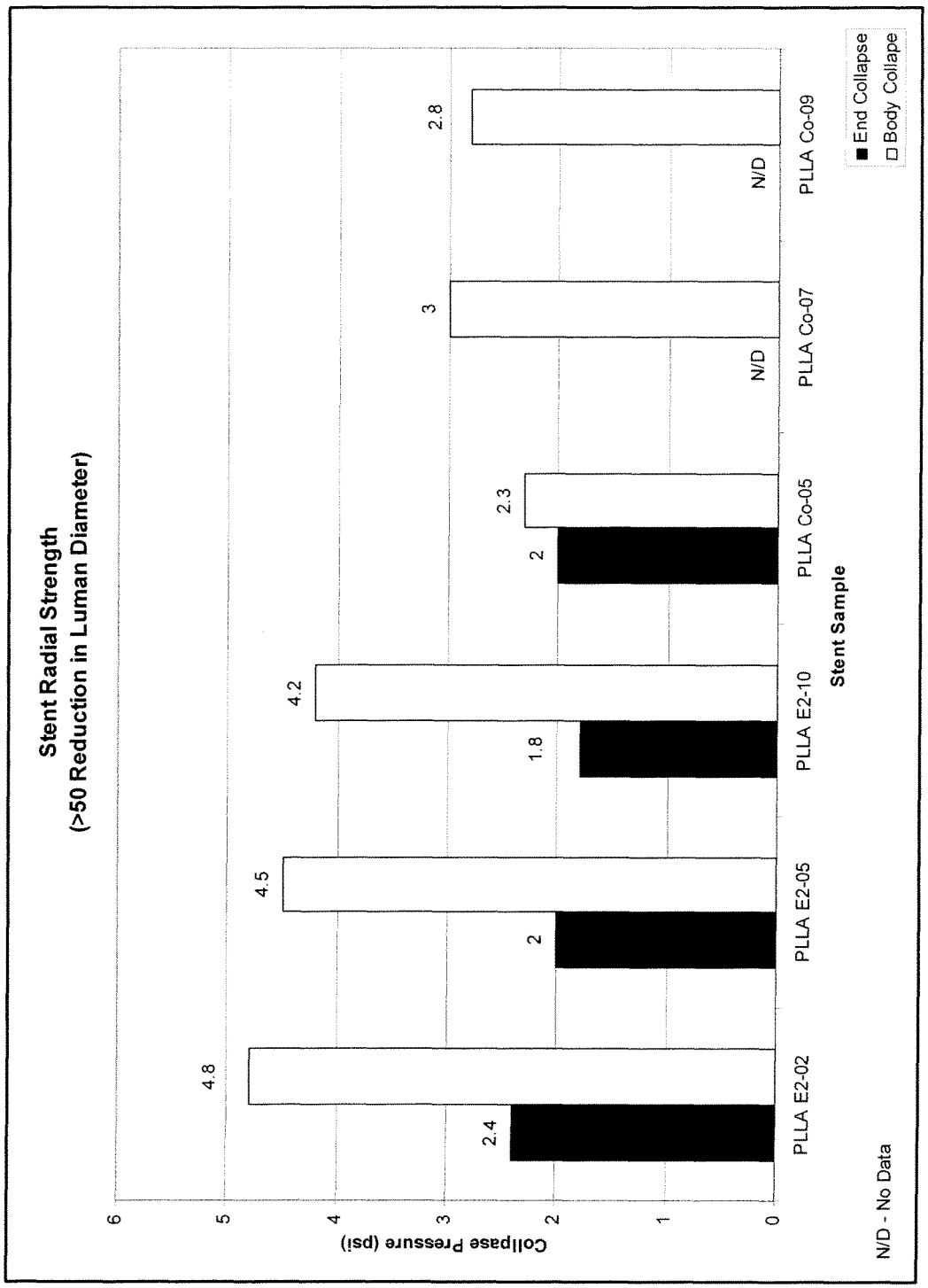
FIG. 17 is a bar graph illustrating data depicting the radial strength of bioabsorbable stents.
Figure 18:
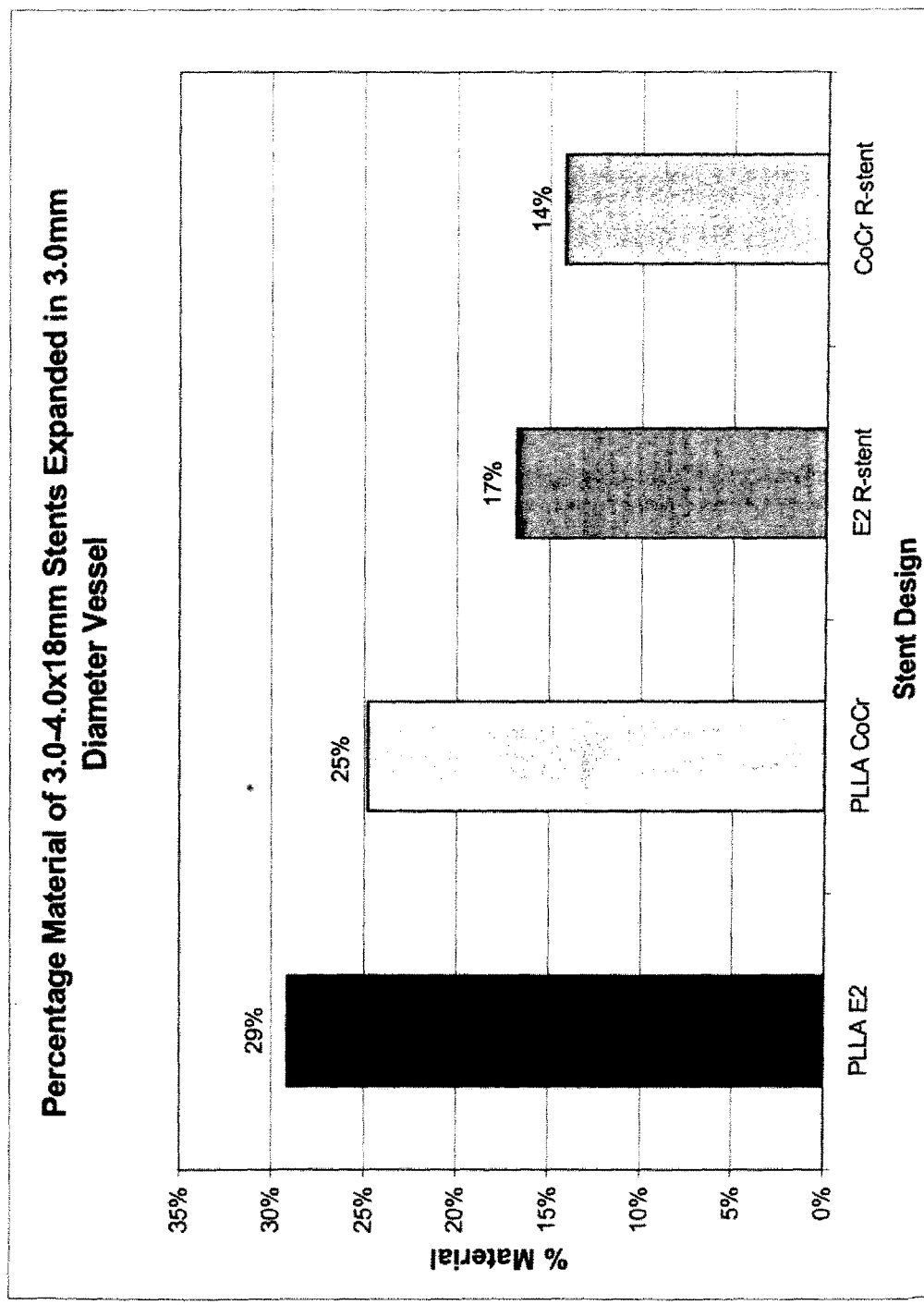
FIG. 18 illustrates is a bar graph illustrating data depicting the percent material of bioabsorbable stents expanded in blood vessels.
Figure 19:
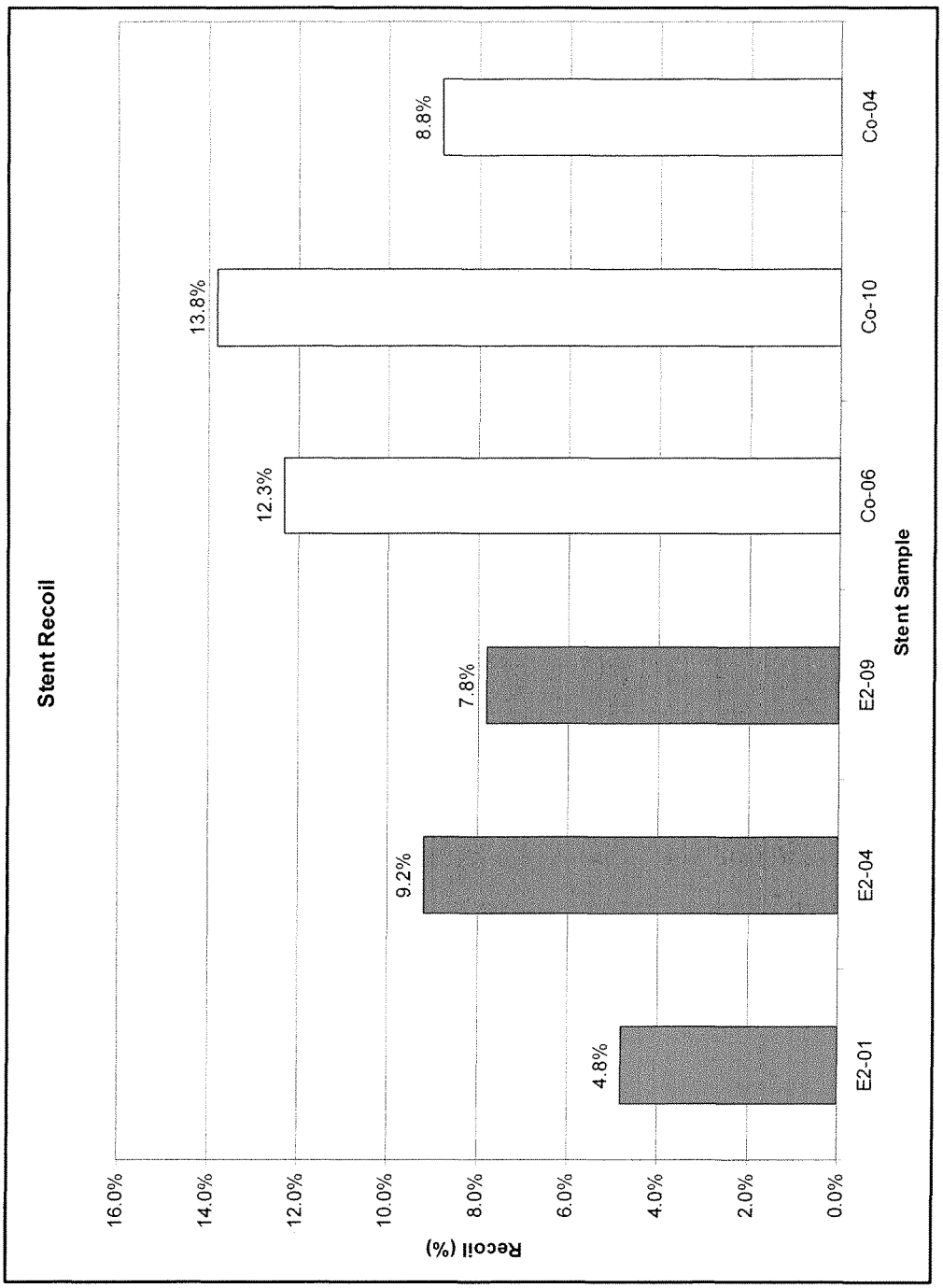
FIG. 19 is a bar graph illustrating data depicting percent stent recoil.
Figure 20:
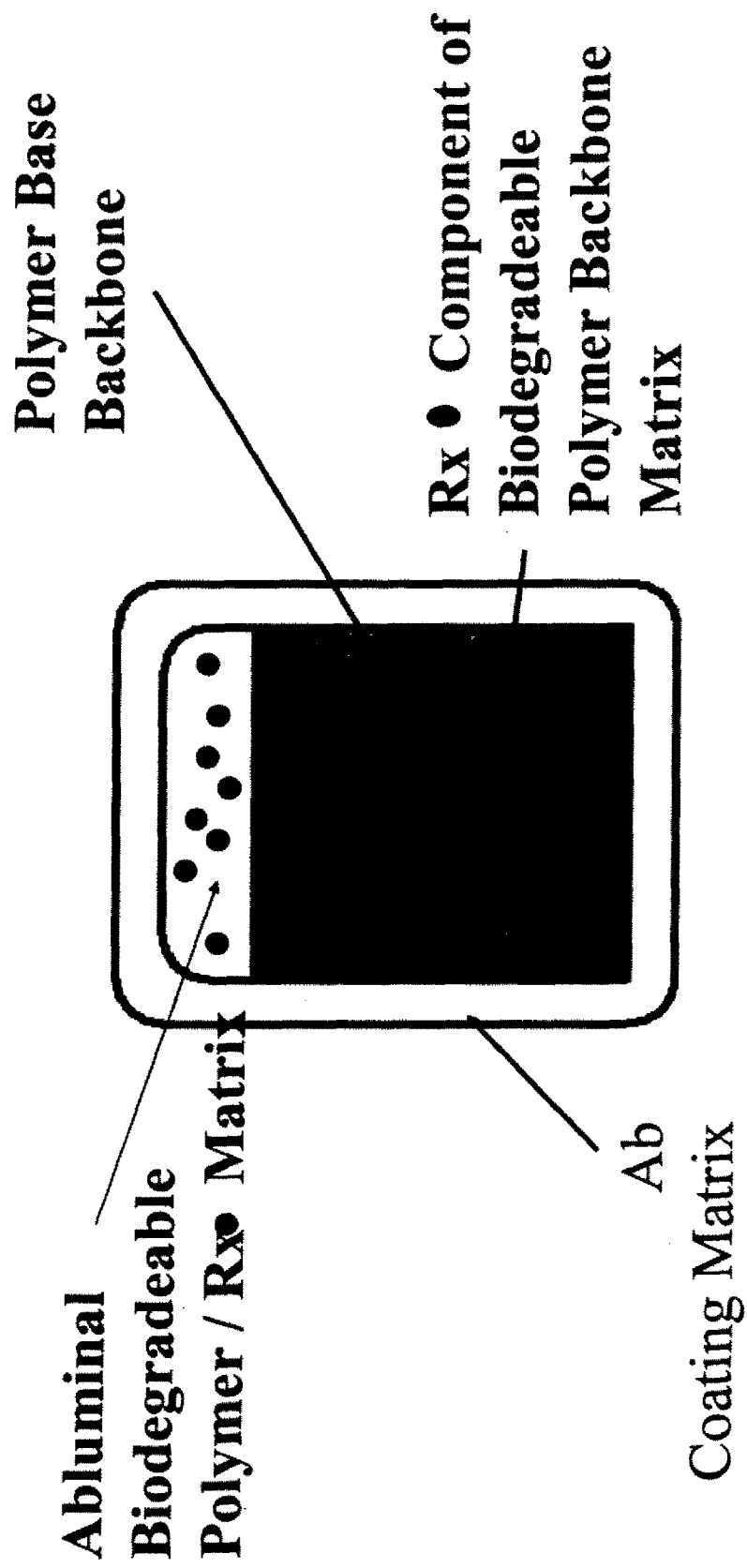
FIG. 20 illustrates a schematic representation of a bioabsorbable stent strut in cross section, which comprises a stent configuration having encapsulated pharmaceutical composition within the struts. In this embodiment, the stent is coated with a matrix comprising an antibody coating and a drug-coated abluminal surface of the device. (Program goal to produce a biodegradable, Abluminal Focused Drug Eluting (RxTBD), Coated Platform. Should the Rx(s) component be integral throughout?)

Various embodiments of biodegradable polymeric stents, and/or stent walls with different configuration are illustrated in FIGS. 1-15. For example, the stent is a tubular structure comprising struts operably designed to allow blood to traverse its walls so that the adjacent tissues are bathed or come in contact with it as blood flows through the area. The particular stent designs selected may depend on the size of the stent radially and longitudinally. FIG. 11A illustrates a scaffold wherein a number of looped structures are positioned above a collapsible/expandable suspension strut as illustrated in FIG. 11A the looped structures a . . . an expand along an axis and suspension strut b is expanded along the same axis. Suspension strut b may be constructed so as to form a closed loop, such as a circumferential loop as shown at FIGS. 11A and 11B; and FIG. 12A and FIG. 12B. The cross-linking strut of the unrolled scaffold of FIG. 11a may maintain higher loop strength. FIG. 15 shows a tube structure embodiment employing such technology; other shapes such as conical, or bifurcated, are also envisioned.

Scaffolds of the present inventions may find employment in many biological areas including, without limitation, the trachea, brachial, fallopian tube, esophagus, and vasculature. Scaffolds may comprise or may be coated with, any type of drug such as hormones, serp-1, MPA etc.

Scaffold elements may be configured to prematurely deform to their maximum length and/or structure and then plastically elongate to form or create a second structure within which has different mechanical properties when compared to the primary structure of the composite structure. Over stretching of the structure may be advantageous to enable alignment of crystalline structures, thereby increasing structural strength. The secondary structure within the primary structure may allow, for example, a bifurcated shape. The secondary structure would allow changes in structures beyond that allowed by simple plastic deformation.

A method of the invention comprises a method for making a bioabsorbable polymeric implant comprising: (a) blending a polymer composition comprising a crystallizable composition comprising a base polymer of poly L-lactide or poly D-lactide linked with modifying copolymers comprising poly L (or D)-lactide-co-Tri-methylene-carbonate or poly L (or D)-lactide-co-e-caprolactone in the form of block copolymers or as blocky random copolymers wherein the lactide chain length is sufficiently long enough to allow cross-moiety crystallization; (b) molding said polymer composition to structurally configure said implant; and (c) cutting said implant.

In one embodiment, the blended form is molded in the form of a tube defining a lumen therein. The tube may then be cut using laser, air knife, or mechanical means, or the like, to form the desired design, such as a stent scaffold. In another embodiment, the blended form is molded into sheets. The sheets are then cut using a laser, air knife, or mechanical means, or the like, to the desired design. If desired, the designed cut sheet may then be welded, annealed, engaged, etc. with another portion of the sheet to form the overall structure desired. For example, the designed, cut, sheet may be rolled into a tubular form and welded along a seam, forming a tube that may later be cut into stents, etc. The sheet itself may be coated on one or both sides with a material, in particular a composition comprising a biological or pharmacological agent. One side may have a coating formed of a different matrix and/or different biological or pharmacological agent or agents.

A method for fabricating the medical device may comprise: (a) preparing a biodegradable polymeric structure; (b) designing said polymeric structure to be configured to allow for implantation into a patient; (c) cutting said structure into patterns configured to permit traversing of the device through openings and to allow for crimping of the device.

The medical device of the invention can be any device used for implanting into an organ or body part comprising a lumen, and can be, but is not limited to, a stent, a stent graft, a synthetic vascular graft, a heart valve, a catheter, a vascular prosthetic filter, a pacemaker, a pacemaker lead, a defibrillator, a patent foramen ovale (PFO) septal closure device, a vascular clip, a vascular aneurysm occluder, a hemodialysis graft, a hemodialysis catheter, an atrioventricular shunt, an aortic aneurysm graft device or components, a venous valve, a sensor, a suture, a vascular anastomosis clip, an indwelling venous or arterial catheter, a vascular sheath and a drug delivery port. The medical device can be made of numerous bioabsorbable materials depending on the device, biodegradable materials such as polylactide polymers and polyglycolide polymers or copolymers thereof are the most suitable.

In one embodiment, the medical device comprises a coating comprising a matrix which comprises a nontoxic, biocompatible, bioerodible and biodegradable synthetic material. The coating may further comprise one or more pharmaceutical substances or drug compositions for delivering to the tissues adjacent to the site of implantation, and one or more ligands, such as a peptide, small and/or large molecules, and/or antibodies or combinations thereof for capturing and immobilizing progenitor endothelial cells on the blood contacting surface of the medical device.

In one embodiment, the implantable medical device comprises a stent with a coating. In accordance with one embodiment, the stent is an expandable intraluminal endoprosthesis designed and configured to have a surface for attaching a coating for controlled or slow release of a therapeutic substance to adjacent tissues.

In one embodiment, the controlled-release matrix can comprise one or more polymers and/or oligomers from various types and sources, including, natural or synthetic polymers, which are biocompatible, biodegradable, bioabsorbable and useful for controlled-released of the medicament. For example, in one embodiment, the naturally occurring polymeric materials can include proteins such as collagen, fibrin, tropoelastin, elastin, cross-linked tropoelastin and extracellular matrix component, or other biologic agents or mixtures thereof. In this embodiment of the invention, the naturally-occurring material can be made by genetic engineering techniques from exogenous genes carried by vectors, such as a plasmid vector and engineered into a host, such as a bacterium. In this embodiment, desired polymer proteins such as tropoelastin and elastin can be produced and isolated for use in the matrix. In alternate embodiments, the naturally occurring polymeric matrices can be purified from natural sources by known methods or they can be obtained by chemical synthesis of the protein polymer. In certain embodiments, the naturally occurring material can be chemically modified or synthesized, for example, by cross-linking the material such as proteins, or by methylation, phosphorylation and the like. In another embodiment, the matrix can comprise a denuded blood vessel or blood vessel scaffolds and/or components thereof.

In one embodiment, the matrix may comprise a synthetic material which can include polyesters such as polylactic acid, polyglycolic acid or copolymers and or combinations thereof, a polyanhydride, polycaprolactone, polyhydroxybutyrate valerate, polydixanone, and other biodegradable polymer, or mixtures or copolymers thereof. In this embodiment, the matrix comprises poly(lactide-coglycolide) as the matrix polymer for coating the medical device. In this embodiment, the poly(lactide-co-glycolide) composition comprises at least one polymer of poly-DL-co-glycolide or copolymer or mixtures thereof, and it is mixed together with the pharmaceutical substances to be delivered to the tissues. The coating composition is then applied to the surface of the device using standard techniques such as spraying, dipping, and/or chemical vaporization. Alternatively, the poly(lactide-co-glycolide) (PGLA) solution can be applied as a single layer separating a layer or layers of the pharmaceutical substance(s).

In another embodiment, the coating composition further comprises pharmaceutically acceptable polymers and/or pharmaceutically acceptable carriers, for example, nonabsorbable polymers, such as ethylene vinyl acetate (EVAC) and methylmethacrylate (MMA). The nonabsorbable polymer, for example, can aid in further controlling release of the substance by increasing the molecular weight of the composition thereby delaying or slowing the rate of release of the pharmaceutical substance.

In certain embodiments, the polymer material or mixture of various polymers can be applied together as a composition with the pharmaceutical substance on the surface of the medical device and can comprise a single layer. Multiple layers of composition can be applied to form the coating. In another embodiment, multiple layers of polymer material or mixtures thereof can be applied between layers of the pharmaceutical substance. For example, the layers may be applied sequentially, with the first layer directly in contact with the uncoated surface of the device and a second layer comprising the pharmaceutical substance and having one surface in contact with the first layer and the opposite surface in contact with a third layer of polymer which is in contact with the surrounding tissue. Additional layers of the polymer material and drug composition can be added as required, alternating each component or mixtures of components thereof.

In another embodiment, the matrix may comprise non-polymeric materials such as nanoparticles formed of, for example, metallic alloys or other materials. In this embodiment, the coating on the medical device can be porous and the pharmaceutical substances can be trapped within and between the particles. In this embodiment, the size of the particles can be varied to control the rate of release of the pharmaceutical substance trapped in the particles depending on the need of the patient. In one embodiment, the pharmaceutical composition can be a slow/controlled-release pharmaceutical composition.

Alternatively, the pharmaceutical substance of the coating can be applied as multiple layers of a composition and each layer can comprise one or more drugs surrounded by polymer material. In this embodiment, the multiple layers of pharmaceutical substance can comprise a pharmaceutical composition comprising multiple layers of a single drug; one or more drugs in each layer, and/or differing drug compositions in alternating layers applied. In one embodiment, the layers comprising pharmaceutical substance can be separated from one another by a layer of polymer material. In another embodiment, a layer of pharmaceutical composition may be provided to the device for immediate release of the pharmaceutical substance after implantation.

In one embodiment, the pharmaceutical substance or composition may comprise one or more drugs or substances which can inhibit smooth muscle cell migration and proliferation at the site of implantation, can inhibit thrombus formation, can promote endothelial cell growth and differentiation, and/or can inhibit restenosis after implantation of the medical device. Additionally, the capturing of the progenitor endothelial cells on the luminal surface of the medical device accelerates the formation of a functional endothelium at the site of injury.

Examples of compounds or pharmaceutical compositions which can be incorporated in the matrix, and/or impregnated into the medical device include, but are not limited to prostacyclin, prostacyclin analogs, α-CGRP, α-CGRP analogs or α-CGRP receptor agonists; prazosin; monocyte chemoattractant protein-1 (MCP-1); immunosuppressant drugs such as rapamycin, drugs which inhibit smooth muscle cell migration and/or proliferation, antithrombotic drugs such as thrombin inhibitors, immunomodulators such as platelet factor 4 and CXC-chemokine; inhibitors of the CX3CR1 receptor family; antiinflammatory drugs, steroids such as dihydroepiandrosterone (DHEA), testosterone, estrogens such as 17β-estradiol; statins such as simvastatin and fluvastatin; PPAR-alpha ligands such as fenofibrate and other lipid-lowering drugs, PPAR-delta and PPAR-gamma agonists such as rosiglitazone; PPAR-dual-αγ agonists, LBM-642, nuclear factors such as NF-κβ, collagen synthesis inhibitors, vasodilators such as acetylcholine, adenosine, 5-hydroxytryptamine or serotonin, substance P, adrenomedulin, growth factors which induce endothelial cell growth and differentiation such as basic fibroblast growth factor (bFGF), platelet-derived growth factor (PDGF), endothelial cell growth factor (EGF), vascular endothelial cell growth factor (VEGF); protein tyrosine kinase inhibitors such as Midostaurin and imatinib or any anti-angionesis inhibitor compound; peptides or antibodies which inhibit mature leukocyte adhesion, antibiotics/antimicrobials, and other substances such as tachykinins, neurokinins or sialokinins, tachykinin NK receptor agonists; PDGF receptor inhibitors such as MLN-518 and derivatives thereof, butyric acid and butyric acid derivatives puerarin, fibronectin, erythropoietin, darbepotin, serine proteinase-1 (SERP-1) and the like. The aforementioned compounds and pharmaceutical substances can be applied to the coating on the device alone or in combinations and/or mixtures thereof.

In one embodiment, the implantable medical device can comprise a coating comprising one or more barrier layers in between said one or more layers of matrix comprising said pharmaceutical substances. In this embodiment, the barrier layer may comprise a suitable biodegradable material, including but not limited to suitable biodegradable polymers including: polyesters such as PLA, PGA, PLGA, PPF, PCL, PCC, TMC and any copolymer of these; polycarboxylic acid, polyanhydrides including maleic anhydride polymers; polyorthoesters; poly-amino acids; polyethylene oxide; polyphosphazenes; polylactic acid, polyglycolic acid and copolymers and mixtures thereof such as poly(L-lactic acid) (PLLA), poly(D,L-lactide), polylactic acid-co-glycolic acid), 50/50 (DL-lactide-co-glycolide); polydixanone; polypropylene fumarate; polydepsipeptides; polycaprolactone and co-polymers and mixtures thereof such as poly(D,L-lactide-co-caprolactone) and polycaprolactone co-butylacrylate; polyhydroxybutyrate valerate and blends; polycarbonates such as tyrosine-derived polycarbonates and arylates, polyiminocarbonates, and polydimethyltrimethyl-carbonates; cyanoacrylate; calcium phosphates; polyglycosaminoglycans; macromolecules such as polysaccharides (including hyaluronic acid; cellulose, and hydroxypropylmethyl cellulose; gelatin; starches; dextrans; alginates and derivatives thereof), proteins and polypeptides; and mixtures and copolymers of any of the foregoing. The biodegradable polymer may also be a surface erodable polymer such as polyhydroxybutyrate and its copolymers, polycaprolactone, polyanhydrides (both crystalline and amorphous), maleic anhydride copolymers, and zinc-calcium phosphate. The number of barrier layers that the coating on a device may have depends on the amount of therapeutic needed as dictated by the therapy required by the patient. For example, the longer the treatment, the more therapeutic substance required over a period of time, the more barrier layers to provide the pharmaceutical substance in a timely manner.

In one embodiment, the coating comprises a ligand which is applied to the blood contacting surface of the medical device and the ligand specifically recognizes and binds a desired component or epitope on the surface of target cells in the circulating blood. In one embodiment, the ligand is specifically designed to recognize and bind only the genetically-altered mammalian cell by recognizing only the genetically-engineered marker molecule on the cell membrane of the genetically-altered cells. The binding of the target cells immobilizes the cells on the surface of the device.

In alternate embodiment, the ligand on the surface of the medical device for binding the genetically-altered cell is selected depending on the genetically engineered cell membrane marker molecule. That is, the ligand binds only to the cell membrane marker molecule or antigen which is expressed by the cell from extrachromosomal genetic material provided to the cell so that only the genetically-modified cells can be recognized by the ligand on the surface of the medical device. In this manner, only the genetically-modified cells can bind to the surface of the medical device. For example, if the mammalian cell is an endothelial cell, the ligand can be at least one type of antibody, antibody fragments or combinations thereof; the antibody is specifically raised against a specific target epitope or marker molecule on the surface of the target cell. In this aspect of the invention, the antibody can be a monoclonal antibody, a polyclonal antibody, a chimeric antibody, or a humanized antibody which recognizes and binds only to the genetically-altered endothelial cell by interacting with the surface marker molecule and, thereby modulating the adherence of the cells onto the surface of the medical device. The antibody or antibody fragment of the invention can be covalently or noncovalently attached to the surface of the matrix, or tethered covalently by a linker molecule to the outermost layer of the matrix coating the medical device. In this embodiment, for example, the monoclonal antibodies can further comprises Fab or F(ab')2 fragments. The antibody fragment of the invention comprises any fragment size, such as large and small molecules which retain the characteristic to recognize and bind the target antigen as the antibody.

In another embodiment, the antibody or antibody fragment of the invention recognize and bind antigens with specificity for the mammal being treated and their specificity is not dependent on cell lineage. In one embodiment, for example, in treating restenosis wherein the cells may not be genetically modified to contain specific cell membrane marker molecules, the antibody or fragment is specific for selecting and binding circulating progenitor endothelial cell surface antigen such as CD133, CD34, CD14, CDw90, CD117, HLA-DR, VEGFR-1, VEGFR-2, Muc-18 (CD146), CD130, stem cell antigen (Sca-1), stem cell factor 1 (SCF/c-Kit ligand), Tie-2, MHC such as H-2Kk and HLA-DR antigen.

In another embodiment, the coating of the medical device comprises at least one layer of a biocompatible matrix as described above, the matrix comprises an outer surface for attaching a therapeutically effective amount of at least one type of small molecule of natural or synthetic origin. The small molecule recognizes and interacts with, for example, progenitor endothelial cells in the treatment of restenosis, to immobilize the cells on the surface of the device to form an endothelial layer. The small molecules can be used in conjunction with the medical device for the treatment of various diseases, and can be derived from a variety of sources such as cellular components such as fatty acids, proteins, nucleic acids, saccharides and the like and can interact with an antigen on the surface of a progenitor endothelial cell with the same results or effects as an antibody. In this aspect of the invention, the coating on the medical device can further comprise a compound such as a growth factor as described herewith in conjunction with the coating comprising an antibody or antibody fragment.

In another embodiment, the coating of the medical device comprises at least one layer of a biocompatible matrix as described above, the matrix comprising a luminal surface for attaching a therapeutically effective amount of at least one type of small molecule of natural or synthetic origin. The small molecule recognizes and interacts with an antigen on the target cell such as a progenitor endothelial cell surface to immobilize the progenitor endothelial cell on the surface of the device to form endothelium. The small molecules can be derived from a variety of sources such as cellular components including, fatty acids, peptides, proteins, nucleic acids, saccharides and the like and can interact, for example, with a structure such as an antigen on the surface of a progenitor endothelial cell with the same results or effects as an antibody.

In another embodiment, there is provided a method for treating vascular disease such as restenosis and artherosclerosis, comprising administering a pharmaceutical substance locally to a patient in need of such substance. The method comprises implanting into a vessel or hollowed organ of a patient a medical device with a coating, which coating comprises a pharmaceutical composition comprising a drug or substance for inhibiting smooth muscle cell migration and thereby restenosis, and a biocompatible, biodegradable, bioerodible, nontoxic polymer or non-polymer matrix, wherein the pharmaceutical composition comprises a slow or controlled-release formulation for the delayed release of the drug. The coating on the medical device can also comprise a ligand such as an antibody for capturing cells such as endothelial cells and or progenitor cells on the luminal surface of the device so that a functional endothelium is formed.

In another embodiment, there is provided a method of making a coated medical device or a medical device with a coating, which comprises applying to a surface of a medical device a polymer or non-polymer matrix and a pharmaceutical composition comprising one or more drugs, and applying a ligand to the medical device so that the ligand attaches to a surface of the device and is designed to bind molecules on the cell membrane of circulating native or genetically engineered cells. In this embodiment, the polymer matrix comprises a biocompatible, biodegradable, nontoxic polymer matrix such as collagen, tropocollagen, elastin, tropoelastin, cross-linked tropoelastin, poly(lactide-co-glycolide) copolymer, polysaccharides and one or more pharmaceutical substances, wherein the matrix and the substance(s) can be mixed prior to applying to the medical device. In this embodiment, at least one type of ligand is applied to the surface of the device and can be added on top or on the outer surface of the device with the drug/matrix composition in contact with the device surface. The method may alternatively comprise the step of applying at least one layer of a pharmaceutical composition comprising one or more drugs and pharmaceutically acceptable carriers, and applying at least one layer of a polymer matrix to the medical device.

In one embodiment, the matrix can be applied as one or more layers and with or without the pharmaceutical substance, and the ligand can be applied independently to the medical device by several methods using standard techniques, such as dipping, spraying or vapor deposition. In an alternate embodiment, the polymer matrix can be applied to the device with or without the pharmaceutical substance. In this aspect of the invention wherein a polymer matrix is applied without the drug, the drug can be applied as a layer between layers of matrices. In other embodiments, a barrier layer is applied between the layers comprising the pharmaceutical substances.

In one embodiment, the method comprises applying the pharmaceutical composition as multiple layers with the ligand applied on the outermost surface of the medical device so that the ligand such as antibodies can be attached in the luminal surface of the device. In one embodiment, the method for coating the medical device comprises: applying to a surface of said medical device at least one or more layers of a matrix, one or more pharmaceutical substance(s), and a basement membrane component; applying to said at least one layer of said composition on said medical device a solution comprising at least one type of ligand for binding and immobilizing genetically-modified target cells; and drying said coating on the stent under vacuum at low temperatures.

In another embodiment, the coating is comprised of a multiple component pharmaceutical composition within the matrix such as containing a fast release pharmaceutical agent to retard early neointimal hyperplasia/smooth muscle cell migration and proliferation, and a secondary biostable matrix that releases a long acting agent for maintaining vessel patency or a positive blood vessel remodeling agent, such as endothelial nitric oxide synthase (eNOS), nitric oxide donors and derivatives such as aspirin or derivatives thereof, nitric oxide producing hydrogels, PPAR agonist such as PPAR-α ligands, tissue plasminogen activator, statins such as atorvastatin, erythropoietin, darbepotin, serine proteinase-1 (SERP-1) and pravastatin, steroids, and/or antibiotics.

The figures provided herewith depict embodiments that are described as illustrative examples that are not deemed in any way as limiting the present invention.

While the invention has been particularly shown and described with reference to particular embodiments, it will be appreciated that variations of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

We claim:
1. A method for making a polymeric scaffold comprising the steps of:
blending a polymer composition comprising a crystallizable polymer composition comprising a base polymer of poly L-lactide, and/or poly D-lactide, and/or poly L-lactide-co-PEG, and/or poly D-lactide-co-PEG, linked with modifying copolymers comprising poly L (or D)-lactide-co-ε-caprolactone in the form of block copolymers or as blocky random copolymers; and
molding or extruding the polymer composition to produce a scaffold;
wherein the polymer composition is crystallizable when the scaffold is expanded.
2. The method of claim 1, wherein the blending further comprises blending a pharmacological and/or biological agent into the polymer composition.
3. The method of claim 2, wherein the pharmacological agent is selected from the group consisting of: cyclosporin A, mycophenolic acid, mycophenolate mofetil acid, rapamycin, rapamycin derivatives, biolimus A9, CCI-779, RAD 001, AP23573, azathioprine, tacrolimus (FK506), tranilast, dexamethasone, corticosteroid, everolimus, pimecrolimus, retinoic acid, vitamin E, rosiglitazone, simvastatins, fluvastatin, estrogen, 17β-estradiol, hydrocortisone, acetaminophen, ibuprofen, naproxen, fluticasone, clobetasol, adalimumab, sulindac, dihydroepiandrosterone, testosterone, puerarin, platelet actor 4, basic fibroblast growth factor, fibronectin, butyric acid, butyric acid derivatives, paclitaxel, paclitaxel derivatives, LBM-642, deforolimus, and probucol.
4. The method of claim 2, wherein the biological agent is selected from the group consisting of: antibiotics/antimicrobials, antiproliferative agents, antineoplastic agents, antioxidants, endothelial cell growth factors, smooth muscle cell growth and/or migration inhibitors, thrombin inhibitors, immunosuppressive agents, anti-platelet aggregation agents, collagen synthesis inhibitors, therapeutic antibodies, nitric oxide donors, antisense oligonucleotides, would healing agents, therapeutic gene transfer constructs, peptides, proteins, extracellular matrix components, vasodilators, thrombolytics, anti-metabolites, growth factor agonists, antimitotics, steroids, steroidal antiinflammatory agents, chemokines, proliferator-activated receptor-gamma agonists, proliferator-activated receptor-alpha agonists proliferator-activated receptor-beta agonists, proliferator-activated receptor-alpha-beta agonists, proliferator-activated receptor-delta agonists, NFκβ, proliferator-activated receptor-alpha-gamma agonists, nonsteroidal antiinflammatory agents, angiotensin converting enzyme (ACE) inhibitors, free radical scavengers, inhibitors of the CX3CR1 receptor and anti-cancer chemotherapeutic agents.
5. The method of claim 1, wherein the blending further comprises blending radio-opaque or radio-detectable material into the polymer composition.

* * * * *